US007244735B2

(12) United States Patent
Straub et al.

(10) Patent No.: US 7,244,735 B2
(45) Date of Patent: Jul. 17, 2007

(54) HETEROCYCLIC PROTEIN KINASE INHIBITORS AND USES THEREOF

(75) Inventors: Judith Straub, Santa Cruz, CA (US); Michael Hale, Bedford, MA (US); Francois Maltais, Tewksbury, MA (US); Gabriel Martinez-Botella, W. Roxbury, MA (US); Alex Aronov, Watertown, MA (US); Guy Bemis, Arlington, MA (US)

(73) Assignee: Vertex Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 11/001,760

(22) Filed: Dec. 2, 2004

(65) Prior Publication Data

US 2005/0245499 A1 Nov. 3, 2005

Related U.S. Application Data

(60) Provisional application No. 60/526,309, filed on Dec. 2, 2003.

(51) Int. Cl.
*A61K 31/496* (2006.01)
*A61K 31/506* (2006.01)
*C07D 239/48* (2006.01)

(52) U.S. Cl. .................. 514/252.14; 514/275; 544/323

(58) Field of Classification Search ................. 544/324, 544/323; 514/252.14, 275
See application file for complete search history.

(56) References Cited

U.S. PATENT DOCUMENTS 4,980,350 A * 12/1990 MacCoss et al. ............ 514/245
2003/0092714 A1 5/2003 Cao et al. .................... 514/242

FOREIGN PATENT DOCUMENTS

DE 19962936 A1 6/2001
WO WO 02/045652 A3 6/2002
WO WO 2003032997 A1 * 4/2003

OTHER PUBLICATIONS

Grossbard, M. L. The Oncologist 1999, 4, 287-292.*
Druker et al. J. Clinical Investigation 2000, 105(1), 3-7.*
Smirne et al. Expert Opin. Ther. Patents 2006, 16(10), pp. 1359-1370.*
Garcia-Echeverria et al. Med. Res. Rev. 20, No. 1, 28-57, 2000.*
* cited by examiner

*Primary Examiner*—Kamal A. Saeed
*Assistant Examiner*—Jason M. Nolan
(74) *Attorney, Agent, or Firm*—Daniel A. Pearson

(57) ABSTRACT

Described herein are compounds that are useful as protein kinase inhibitors of formula I:

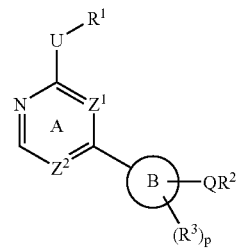

or a pharmaceutically acceptable salt thereof, wherein Ring B, $Z^1$, $Z^2$, U, p, Q, $R^1$, $R^2$, $R^3$, and $R^3$ are as defined herein. These compounds, and pharmaceutically acceptable compositions thereof, are useful for treating or lessening the severity of a variety of disorders, including stroke, inflammatory disorders, autoimmune diseases such as SLE lupus and psoriasis, proliferative disorders such as cancer, and conditions associated with organ transplantation.

13 Claims, No Drawings

HETEROCYCLIC PROTEIN KINASE INHIBITORS AND USES THEREOF

CROSS REFERENCE TO RELATED APPLICATIONS

This application claims priority to U.S. Provisional Patent Application 60/526,309 filed Dec. 2, 2003, the entire contents of which are hereby incorporated herein by reference.

FIELD OF THE INVENTION

The present invention is in the field of medicinal chemistry and relates to pyrimidine compounds that are protein kinase inhibitors, compositions containing such compounds and methods of use. The compounds are useful for treating cancer, neurological disorders, autoimmune disorders, and other diseases that are alleviated by protein kinase inhibitors.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250–300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families.

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor a (TNF-a)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents. However, considering the lack of currently available treatment options for the majority of the conditions associated with protein kinases, there is still a great need for new therapeutic agents that inhibit these protein targets.

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

ERK2 is a widely distributed protein kinase that achieves maximum activity when both Thr183 and Tyr185 are phosphorylated by the upstream MAP kinase kinase, MEK1. Upon activation, ERK2 phosphorylates many regulatory proteins, including the protein kinases Rsk90 and MAP-KAP2, and transcription factors such as ATF2, Elk-1, c-Fos, and c-Myc. ERK2 is also a downstream target of the Ras/Raf dependent pathways and relays the signals from these potentially oncogenic proteins. ERK2 has been shown to play a role in the negative growth control of breast cancer cells and hyperexpression of ERK2 in human breast cancer has been reported. Activated ERK2 has also been implicated in the proliferation of endothelin-stimulated airway smooth muscle cells, suggesting a role for this kinase in asthma.

Overexpression of receptor tyrosine kinases such as EGFR and ErbB2, as well as activating mutations in the Ras GTPase proteins or B-Raf mutants are major contributors to human cancer. These genetic alterations are correlated with poor clinical prognosis and result in activation of the Raf-1/2/3-MEK1/2-ERK1/2 signal transduction cascade in a broad panel of human tumors. Activated ERK (i.e. ERK1 and/or ERK2) is a central signaling molecule that has been associated with the control of proliferation, differentiation, anchorage-independent cell survival, and angiogenesis, contributing to a number of processes that are important for the formation and progression of malignant tumors. These data suggest that an ERK1/2 inhibitor will exert pleiotropic activity, including proapoptotic, anti-proliferative, anti-metastatic and anti-angiogenic effects, and offer a therapeutic opportunity against a very broad panel of human tumors.

There is a growing body of evidence that implicates constitutive activation of the ERK MAPK pathway in the oncogenic behavior of select cancers. Activating mutations of Ras are found in ~30% of all cancers, with some, such as pancreatic (90%) and colon (50%) cancer, harboring particularly high mutation rates (ref). Ras mutations have also been identified in 9–15% of melanomas, but B-Raf somatic missense mutations conferring constitutive activation are more frequent and found in 60–66% malignant melanomas. Activating mutations of Ras, Raf and MEK are able to oncogenically transform fibroblasts in vitro, and Ras or Raf mutations in conjunction with the loss of a tumor suppressor gene (e.g. p16INK4A) can cause spontaneous tumor development in vivo. Increased ERK activity has been demonstrated in these models and has also been widely reported in appropriate human tumors. In melanoma, high basal ERK activity resulting from either B-Raf or N-Ras mutations or autocrine growth factor activation is well documented and has been associated with rapid tumor growth, increased cell survival and resistance to apoptosis. Additionally, ERK activation is considered a major driving force behind the highly metastatic behavior of melanoma associated with increased expression of both extracellular matrix degrading proteases and invasion-promoting integrins as well as the downregulation of E-cadherin adhesion molecules that normally mediate keratinocyte interactions to control melanocyte growth. These data taken together, indicate ERK as promising therapeutic target for the treatment of melanoma, a currently untreatable disease.

Glycogen synthase kinase-3 (GSK-3) is a serine/threonine protein kinase comprised of α and β isoforms that are each encoded by distinct genes. GSK-3 has been implicated in various diseases including diabetes, Alzheimer's disease, CNS disorders such as manic depressive disorder and neurodegenerative diseases, and cardiomyocyte hypertrophy. These diseases are associated with the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPBα. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake. However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that GSK-3 is overexpressed in patients with type II diabetes. Therapeutic inhibitors of GSK-3 are therefore useful for treating diabetic patients suffering from an impaired response to insulin.

Apoptosis has been implicated in the pathophysiology of ischemic brain damage. Recent publications indicate that activation of GSK-3β may be involved in apoptotic mechanisms. Studies in rat models of ischemic stroke induced by middle cerebral artery occlusion (MCAO) showed increased GSK-3β expression is following ischemia. Fibroblast growth factor (FGF) reduced ischemic brain injury after permanent middle cerebral artery occlusion (MCO) in rats. Indeed, the neuroprotective effects of FGF demonstrated in ischemia models in rats may be mediated by a PI-3 kinase/AKT-dependent inactivation of GSK-3β. Thus, inhibition of GSK-3β after a cerebral ischemic event may ameliorate ischemic brain damage.

GSK-3 is also implicated in mycardial infarction, head trauma, and psychiatric disorders. It has been shown that GSK3 inhibition by lithium and valproic acid induces axonal remodeling and change synaptic connectivity.

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells. In transgenic mice overexpressing GSK3, significant increased Tau hyperphosphorylation and abnormal morphology of neurons were observed. Active GSK3 accumulates in cytoplasm of pretangled neurons, which can lead to neurofibrillary tangles in brains of patients with AD. Therefore, inhibition of GSK-3 slows or halts the generation of neurofibrillary tangles and thus treats or reduces the severity of Alzheimer's disease.

Evidence for the role GSK-3 plays in Alzheimer's disease has been shown in vitro and in vivo. Presenilin-1 and kinesin-1 are also substrates for GSK-3 and relate to another mechanism for the role GSK-3 plays in Alzheimer's disease. It was found that GSK3beta phosphorylates kinesin-I light chain, which results in a release of kinesin-1 from membrane-bound organelles, leading to a reduction in fast anterograde axonal transport. The authors suggest that the mutations in PS1 may deregulate and increase GSK-3 activity, which in turn, impairs axonal transport in neurons. The consequent reductions in axonal transport in affected neurons ultimately lead to neurodegeneration.

GSK-3 is also associated with amyotrophic lateral sclerosis (ALS). GSK-3 activity is also linked to spinal cord and peripheral nerve injuries. It has been shown that GSK3 inhibition by lithium and valproic acid can induce axonal remodeling and change synaptic connectivity.

Another substrate of GSK-3 is β-catenin, which is degraded after phosphorylation by GSK-3. Reduced levels of β-catenin have been reported in schizophrenic patients and have also been associated with other diseases related to increase in neuronal cell death. Furthermore, β-catenin and Tcf-4 play a dual role in vascular remodeling by inhibiting vascular smooth muscle cell apoptosis and promoting proliferation. Accordingly, GSK-3 is associated with angiogenic disorders.

Association between GSK-3 and Huntington's disease has been shown. Overexpression of GSK3 reduced the activation of heat shock transcription factor-1 and heat shock protein HSP70 that are shown to decrease both poly-(Q) aggregates and cell death in in vitro HD model.

GSK-3 effects the levels of FGF-2 and their receptors are increased during remyelination of brain aggregate cultures remyelinating rat brains. It was also found that FGF-2 induces process outgrowth by oligodendrocytes implicating involvement of FGF in remyelination and that FGF-2 gene therapy has shown to improve the recovery of experimental allergic encephalomyelitis (EAE) mice.

GSK-3 has also been associated with hair growth because Wnt/beta-catenin signaling is shown to play a major role in hair follicle morphogenesis and differentiation. It was found that mice with constitutive overexpression of the inhibitors of Wnt signaling in skin failed to develop hair follicles. Wnt signals are required for the initial development of hair follicles and GSK3 constitutively regulates Wnt pathways by inhibiting beta-catenin. A transient Wnt signal provides the crucial initial stimulus for the start of a new hair growth cycle, by activating beta-catenin and TCF-regulated gene transcription in epithelial hair follicle precursors.

Because GSK-3 activity is associated with sperm motility, GSK-3 inhibition is useful as a male contraceptive. It was shown that a decline in sperm GSK3 activity is associated with sperm motility development in bovine and monkey epididymis. Furthermore, tyrosine & serine/threonine phosphorylation of GSK3 is high in motile compared to immotile sperm in bulls. This effect was also demonstrated with human sperm.

Cyclin-dependent kinases (CDKS) are serine/threonine protein kinases consisting of a b-sheet rich amino-terminal lobe and a larger carboxy-terminal lobe that is largely a-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active.

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases.

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the overexpression of cyclin D1 is commonly associated with numerous human cancers including breast, colon, hepatocellular carcinomas and gliomas. The CDK2/cyclin E complex plays a key role in the progression from the early G1 to S phases of the cell cycle and the overexpression of cyclin E has been associated with various solid tumors. Therefore, inhibitors of cyclins D1, E, or their associated CDKs are useful targets for cancer therapy.

CDKs, especially CDK2, also play a role in apoptosis and T-cell development. CDK2 has been identified as a key regulator of thymocyte apoptosis. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegalovirus, herpes virus, and varicella-zoster virus.

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25.

PIM-1 is the protooncogene activated by murine leukemia virus (Provirus Integration site for Moloney murine leukemia virus). The expression of the protoconcogene produces a non-transmembrane serine/threonine kinase of 313 residues, including a kinase domain consisting of 253 amino acid residues. Two isoforms are known through alternative initiation (p44 and p33). Two PIM-1 homologs have been described. PIM-2 and PIM-3 are respectively 58% and 69% identical to Pim-1 at the amino acid level. PIM-1 is highly expressed in the liver and spleen during hematopoiesis, and expression is induced by cytokines such as GM-CSF, G-SCF, IL-3, IF-α, and IL-6.

Another kinase family of interest is Rho-associated coiled-coil forming protein serine/threonine kinase (ROCK), which is believed to be an effector of Ras-related small GTPase Rho. The ROCK family includes p160ROCK (ROCK-1) and ROKα/Rho-kinase/ROCK-II, protein kinase PKN, and citron and citron kinase. The ROCK family of kinases have been shown to be involved in a variety of functions including Rho-induced formation of actin stress fibers and focal adhesions and in downregulation of myosin phosphatase, aortic smooth muscle contraction by various stimuli, thrombin-induced responses of aortic smooth muscle cells, hypertrophy of cardiomyocytes, bronchial smooth muscle contraction, smooth muscle contraction and cytoskeletal reorganization of non-muscle cells, activation of volume-regulated anion channels, neurite retraction, neutrophil chemotaxis, wound healing, tumor invasion and cell transformation. Accordingly, the development of inhibitors of ROCK kinase would be useful as therapeutic agents for the treatment of disorders mediated by the ROCK kinase pathway.

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed.

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling.

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions. A crucial role for JAK3 in IgE receptor-mediated mast cell responses in vitro and in vivo has been established. In addition, the prevention of type I hypersensitivity reactions, including anaphylaxis, mediated by mast cell-activation through inhibition of JAK3 has also been reported. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease.

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demonstrated that IL-4-mediated activation of IL-4/STAT pathway is mediated through the Janus Kinases (JAK 1 & 3) and that IL-4-associated JAK kinases are expressed in the RA synovium.

Familial amyotrophic lateral sclerosis (FALS) is a fatal neurodegenerative disorder affecting about 10% of ALS patients. The survival rates of FALS mice were increased upon treatment with a JAK3 specific inhibitor. This confirmed that JAK3 plays a role in FALS.

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth.

Inhibition of JAK 3 and TYK 2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth. In addition, IL-6 —mediated STAT3 activation was blocked by an inhibitor of JAK, leading to sensitization of myeloma cells to apoptosis.

As a result of the biological importance of protein kinases, there is current interest in therapeutically effective protein kinase inhibitors. Accordingly, there is still a great need to develop inhibitors of protein kinases that are useful in treating various diseases or conditions associated with protein kinase activation.

SUMMARY OF THE INVENTION

It has now been found that compounds of this invention, and compositions thereof, are effective as protein kinase inhibitors. In certain embodiments, the present compounds are inhibitors of ERK2, GSK3, ROCK, JAK3, and/or CDK. These compounds have the general formula I:

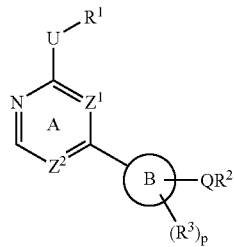

or a pharmaceutically acceptable salt thereof, wherein Ring B, $Z^1$, $Z^2$, U, p, Q, $R^1$, $R^2$, $R^3$, and $R^3$ are as defined below.

These compounds, and pharmaceutically acceptable compositions thereof, are useful for treating or lessening the severity of a variety of disorders, including stroke, Alzheimer's disease, immunodeficiency disorders, inflammatory diseases, allergic diseases, autoimmune diseases, inflammatory disorders, proliferative disorders such as cancer, and conditions associated with organ transplantation.

DESCRIPTION OF THE INVENTION

I. General Description of Compounds of the Invention:
The present invention provides a compound of formula I:

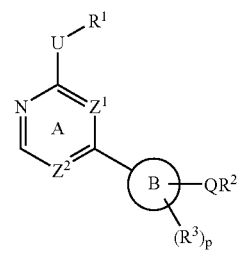

or a pharmaceutically acceptable salt thereof, wherein:
Ring B is a 3–7 membered saturated ring having 0–3 heteroatoms independently selected from nitrogen, oxygen, or sulfur;
$Z^1$ is nitrogen or $CR^x$;
$R^x$ is selected from R, halogen, CN, $NO_2$, OR, SR, $N(R)_2$, C(O)R, or $CO_2R$, or:
$R^x$ and U-$R^1$ are taken together to form an optionally substituted 5–7 membered saturated, partially unsaturated, or fully unsaturated ring having 0–2 heteroatoms independently selected from nitrogen, oxygen, or sulfur;
$Z^2$ is nitrogen or $C$-$T_{(m)}R^y$;
T and Q are each independently selected from a saturated or unsaturated $C_{1-6}$ alkylidene chain wherein:
up to two methylene units of the chain are optionally and independently replaced by —C(O)—, —C(O)C(O)—, —C(O)NR—, —C(O)NRNR—, —$CO_2$—, —OC(O)—, —$NRCO_2$—, —O—, —NRC(O)NR—, —OC(O)NR—, —NRNR—, —NRC(O)—, —S—, —SO—, —$SO_2$—, —NR—, —$SO_2$NR—, or —$NRSO_2$—;
m is zero or one;
each R is independently selected from hydrogen or an optionally substituted $C_{1-6}$ aliphatic group, or:
two R on the same nitrogen are taken together with the nitrogen to form a 5–8 membered heterocyclyl or heteroaryl ring having 1–3 heteroatoms independently selected from nitrogen, oxygen, or sulfur;
$R^y$ is selected from CN, halogen, $N(R)_2$, OR, R, or Ar;
each Ar is an optionally substituted ring selected from a 6–10 membered aryl ring, a 5–10 membered heteroaryl ring having 1–4 heteroatoms independently selected from nitrogen, oxygen, or sulfur, or a 3–10 membered heterocyclyl ring having 1–4 heteroatoms independently selected from nitrogen, oxygen, or sulfur;
$R^1$ is selected from CN, R, Ar, —$(CH_2)_y$CH($R^4$)$R^5$, or —$(CH_2)_y$CH($R^4$)Ch($R^5$)$_2$;
each y is independently 0–6;
U is selected from a valence bond, —O—, —S—, —N(R)—, or a $C_{1-6}$ alkylidene chain wherein up to two methylene units of U are optionally and independently replaced by —O—, —S—, —SO—, —$SO_2$—, —N(R)$SO_2$—, —$SO_2$N(R)—, —N(R)—, —CO—, —$CO_2$—, —N(R)CO—, —N(R)C(O)O—, —N(R)CON(R)—, —N(R)$SO_2$N(R)—, —N(R)N(R)—, —C(O)N(R)—, or —OC(O)N(R)—;

$R^2$ is selected from $(CH_2)_yCH(R^5)_2$ or $(CH_2)_yCH(R^4)CH(R^5)_2$;

y is 0–6;

$R^3$ is selected from oxo, R, F, Cl, $N(R)_2$, OR, SR, NRC(O)R, $NRC(O)N(R)_2$, $C(O)N(R)_2$, $SO_2R$, $NRSO_2R$, C(O)R, CN, $SO_2N(R)_2$, N(R)O, ON(R), or N(R)N(R);

p is 0–4;

$R^4$ is selected from R, $(CH_2)_wOR$, $(CH_2)_wN(R)_2$, or $(CH_2)_wSR$;

w is 0–4; and each $R^5$ is independently selected from optionally substituted $C_{1-6}$ aliphatic, Ar, $(CH_2)_wOR$, $CO_2R$, $(CH_2)_wN(R)_2$, N(Ar)(R), $(CH_2)_wSR$, NRC(O)R, $NRC(O)N(R)_2$, $C(O)N(R)_2$, $SO_2R$, $NRSO_2R$, C(O)R, CN, or $SO_2N(R)_2$.

2. Compounds and Definitions:

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$–$C_{12}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$(as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —R°, —OR°, —SR°, 1,2-methylene-dioxy, 1,2-ethylenedioxy, protected OH (such as acyloxy), phenyl (Ph), Ph substituted with R°, —O(Ph), O—(Ph) substituted with R°, —$CH_2$(Ph), —$CH_2$(Ph) substituted with R°, —$CH_2CH_2$(Ph), —$CH_2CH_2$(Ph) substituted with R°, —$NO_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, or —(CH$_2$)$_y$NHC(O)R°, wherein each R° is independently selected from hydrogen, optionally substituted $C_{1-6}$ aliphatic, an unsubstituted 5–6 membered heteroaryl or heterocyclic ring, phenyl (Ph), —O(Ph), or —$CH_2$(Ph)—$CH_2$(Ph). Substituents on the aliphatic group of R° are selected from $NH_2$, NH($C_{1-4}$ aliphatic), N($C_{1-4}$ aliphatic)$_2$, halogen, $C_{1-4}$ aliphatic, OH, O—($C_{1-4}$ aliphatic), $NO_2$, CN, $CO_2H$, $CO_2$($C_{1-4}$ aliphatic), —O(halo $C_{1-4}$ aliphatic), or halo $C_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Substituents on the aliphatic group of R* are selected from $NH_2$, NH($C_{1-4}$ aliphatic), N($C_{1-4}$ aliphatic)$_2$, halogen, $C_{1-4}$ aliphatic, OH, O—($C_{1-4}$ aliphatic), $NO_2$, CN, $CO_2H$, $CO_2$($C_{1-4}$ aliphatic), —O(halo $C_{1-4}$ aliphatic), or halo $C_{1-4}$ aliphatic.

Substituents on the nitrogen of a non-aromatic heterocyclic ring are selected from —$R^+$, —N($R^+$)$_2$, —C(O)$R^+$, —CO$_2R^+$, —C(O)C(O)$R^+$, —C(O)CH$_2$C(O)$R^+$, —SO$_2R^+$, —SO$_2$N($R^+$)$_2$, —C(=S)N($R^+$)$_2$, —C(=NH)—N($R^+$)$_2$, or —$NR^+SO_2R^+$; wherein $R^+$ is hydrogen, an optionally substituted $C_{1-6}$ aliphatic, optionally substituted phenyl (Ph), optionally substituted —O(Ph), optionally substituted —$CH_2$(Ph), optionally substituted —$CH_2CH_2$(Ph), or an unsubstituted 5–6 membered heteroaryl or heterocyclic ring. Substituents on the aliphatic group or the phenyl ring of $R^+$are selected from $NH_2$, NH($C_{1-4}$ aliphatic), N($C_{1-4}$ aliphatic)$_2$, halogen, $C_{1-4}$ aliphatic, OH, O—($C_{1-4}$ aliphatic), $NO_2$, CN, $CO_2H$, $CO_2$($C_{1-4}$ aliphatic), —O(halo $C_{1-4}$ aliphatic), or halo $C_{1-4}$ aliphatic.

The term "alkylidene chain" refers to a straight or branched carbon chain that may be fully saturated or have one or more units of unsaturation and has two points of connection to the rest of the molecule.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

Compounds of this invention may exist in alternative tautomeric forms. Unless otherwise indicated, the representation of either tautomer is meant to include the other.

3. Description of Exemplary Compounds:

One aspect of the present invention relates to a compound of formula I wherein $(T)_m R^y$, when present, is selected from hydrogen, $N(R)_2$, halogen, OH, 3–6 membered carbocyclyl, or an optionally substituted group selected from $C_{1-6}$ aliphatic, a 6 membered aryl ring, or a 5–6 membered heteroaryl ring having 1–3 heteroatoms independently selected from nitrogen, oxygen, or sulfur. When $R^y$ is an optionally substituted phenyl or aliphatic group, preferred substituents on the phenyl or aliphatic group are $R^o$, halo, nitro, alkoxy, and amino. Examples of such $(T)_m R^y$ groups include chloro, fluoro, methyl, ethyl, propyl, cyclopropyl, cyclohexyl, $CH_2OCH_3$, $CH_2OH$, $NH_2$, $NHCH_3$, NHAc, NHC(O) $NHCH_3$, and $CH_2NHCH_3$.

According to another embodiment, the present invention relates to a compound of formula I wherein $R^1$ is selected from hydrogen, R, optionally substituted 3–7 membered carbocyclyl or an optionally substituted group selected from a 3–6 membered heterocyclic ring having 1–3 heteroatoms independently selected from nitrogen, oxygen, or sulfur, or a 5–6 membered aryl or heteroaryl ring having 1–3 heteroatoms independently selected from nitrogen, oxygen, or sulfur. Examples of such groups include methyl, ethyl, propyl, isopropyl, isobutyl, cyclopropyl, cyclohexyl, 4-hydroxycyclohexyl, phenyl, benzyl, isoxazolyl, tetrahydrofuranyl, Et, Me, isopropyl, $CH_2$cyclopropyl, isoxazol-3-yl, pyridyl, and isopropyl. When $R^1$ is optionally substituted phenyl, substituents on the phenyl ring include halogen, $R^o$, $OR^o$, $N(R^o)_2$, $CO_2R^o$, and $SO_2N(R^o)_2$. Examples of such substituents include fluoro, $NH_2$, Cl, Br, $OCH_2$phenyl, morpholin-4-yl, $CO_2Me$, OMe, haloalkyl (e.g. $CF_3$), Obenzyl, Ophenyl, $OCF_3$, OH, $SO_2NH_2$, and methylene dioxy. When $R^1$ is $-(CH_2)_y CH(R^5)_2$, examples of such groups include $-CH(CH_3)CH_2OH$, $-CH_2$pyridyl, $-CH(CH_2OH)$phenyl, $-CH(CH_2OH)$ethyl, $-CH(CH_2OH)_2$, $-CH(CH_2OH)$isopropyl, and $-CH(CH_2OH)CH_2$cyclopropyl.

U groups of formula I include a valence bond, $-CH_2-$, $-O-$, $-NR-$, $-NHC(O)-$, and $-NHCO_2-$.

According to one embodiment, the U group of formula I is $-NR-$.

According to another embodiment, the U group of formula I is a valence bond.

Yet another embodiment of the present invention relates to a compound of formula I wherein U is $-O-$.

The Q group of formula I includes a $C_{1-4}$ alkylidene chain wherein one or two methylene units of Q are independently replaced by $-C(O)-$, $-OC(O)-$, $-C(O)NH-$, $-OC(O)NH-$, $-SO_2-$, $-SO_2NH-$, $-NHC(O)-$, $-NHC(O)O-$, or $-NHSO_2-$.

According to one embodiment, the Q group of formula I is $-C(O)-$, $-SO_2-$, $-C(O)NH-$, or $-SO_2NH-$.

Another embodiment relates to a compound of formula I wherein Q is $-C(O)-$ or $-C(O)NH-$.

Yet another embodiment of the present invention relates to a compound of formula I wherein Q is NHC(O).

According to another embodiment, when $R^2$ of formula I is $-(CH_2)_y CH(R^5)_2$, each $R^5$ group is independently selected from optionally substituted $C_{1-4}$ aliphatic, $C_{5-6}$ cycloalkyl, phenyl, a 5–9 membered heteroaryl ring having 1–2 heteroatoms independently selected from nitrogen, oxygen, or sulfur, or a 5–6 membered heterocyclic ring having 1–2 heteroatoms independently selected from nitrogen, oxygen, or sulfur. Such $R^5$ groups include those independently selected from pyridin-3-yl, pyridin-4-yl, morpholin-4-yl, thiomorpholin-4-yl, imidazolyl, furan-2-yl, 1,2,3,4-tetrahydroisoquinoline, tetrahydrofuran-2-yl, cyclohexyl, phenyl, benzyl, $-CH_2OH$, $-(CH_2)_2OH$, and isopropyl, wherein each group is optionally substituted. Such substituents on $R^5$ include halogen, $R^o$, $NO_2$, $OR^o$, or $SR^o$. Examples of such substituents are chloro, fluoro, methyl, ethyl, isopropyl, $OCH_3$, $-OH$, $SCH_3$, pyridyl, piperidinyl, and optionally substituted phenyl.

According to yet another embodiment, when $R^2$ of formula I is $-(CH_2)_y CH(R^5)_2$ the $R^5$ groups are selected from $-OR$, $-CO_2R$, $-(CH_2)_w N(R)_2$, or $-N(Ar)(R)$ wherein each R is independently selected from hydrogen or an optionally substituted $C_{1-4}$ aliphatic group and Ar is $C_{5-6}$ cycloalkyl, phenyl, a 5–9 membered heteroaryl ring having 1–2 heteroatoms independently selected from nitrogen, oxygen, or sulfur, or a 5–6 membered heterocyclic ring having 1–2 heteroatoms independently selected from nitrogen, oxygen, or sulfur. Substituents on R include $OR^o$, $-SR^o$, phenyl, $-O(Ph)$, $-CH_2(Ph)$, $-N(R^o)_2$, $-NR^o C(O)R^o$, $-NR^o C(O)N(R^o)_2$, $-NR^o CO_2 R^o$, $-CO_2 R^o$, $-C(O)R^o$, or $-C(O)N(R^o)_2$, wherein each $R^o$ is independently selected from hydrogen, a $C_{1-4}$ aliphatic group, or an unsubstituted 5–6 membered heteroaryl or heterocyclic ring having 1–3 heteroatoms independently selected from nitrogen, oxygen, or sulfur, phenyl (Ph), $-O(Ph)$, or $-CH_2(Ph)-CH_2(Ph)$. Substituents on the aliphatic group of $R^o$ include $NH_2$, $NH(C_{1-4}$ aliphatic), $N(C_{1-4}$ aliphatic)$_2$, halogen, $C_{1-4}$ aliphatic, OH, $O-(C_{1-4}$ aliphatic), $NO_2$, CN, $CO_2H$, $CO_2(C_{1-4}$ aliphatic), $-O$(halo $C_{1-4}$ aliphatic), or halo $C_{1-4}$ aliphatic.

Another aspect of the present invention relates to a compound of formula I wherein $R^2$ is $-(CH_2)_y CH(R^4)CH(R^5)_2$, wherein $R^4$ group is R or OR, such as OH or $CH_2OH$, and wherein $R^5$ is as described above. Such $-(CH_2)_y CH(R^4)CH(R^5)_2$ groups of formula I are $-CH(OH)CH(OH)$phenyl and $-CH(Me)CH(OH)$phenyl. Other $-QR^2$ groups include those listed in Table 2 below.

The present invention relates to a compound of formula I, wherein Ring A is pyridinyl, pyrimidinyl, or triazinyl. Accordingly, the present invention relates to the following compounds of formulae I-a, I-b, I-c, and I-d:

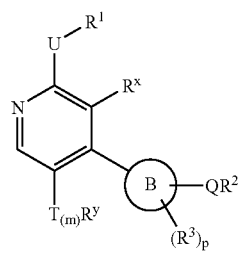

I-a

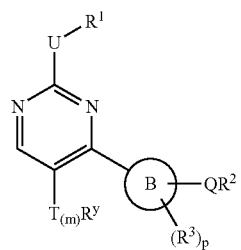

I-b

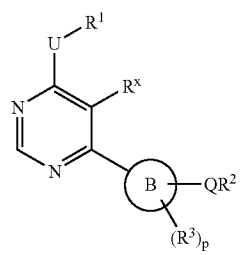

I-c

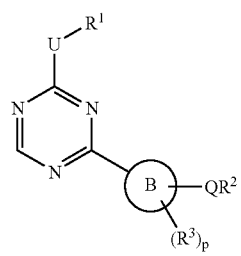

I-d

According to one embodiment, the present invention relates to a compound of formula I wherein Ring B is a 3–7 membered saturated ring having 1–2 nitrogens.

According to another embodiment, the present invention relates to a compound of formula I wherein Ring B is a 4–7 membered saturated ring having 1–2 oxygens.

Yet another embodiment of the present invention relates to a compound of formula I wherein Ring B is a 5–6 membered saturated ring having one oxygen and one nitrogen.

According to another embodiment, the present invention relates to a compound of formula I wherein Ring B is a 3–7 membered saturated ring having zero heteroatoms.

Another aspect of the present invention relates to a compound of formula I wherein Ring B is selected from the Ring B moieties set forth in Table 1 below.

TABLE 1

Ring B Moieties

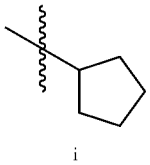

i

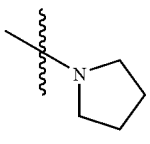

ii

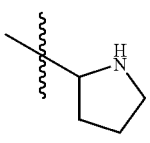

iii

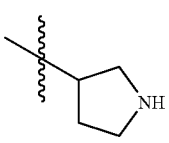

iv

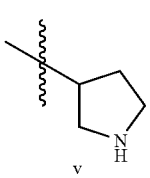

v

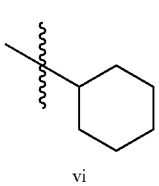

vi

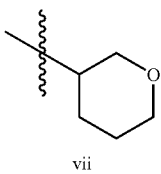

vii

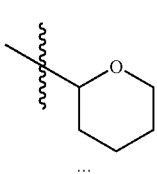

viii

TABLE 1-continued
Ring B Moieties
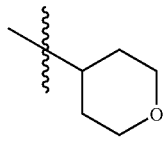
ix
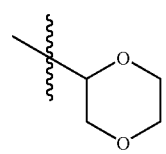
x
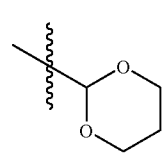
xi
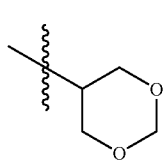
xii
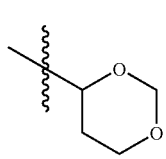
xiii
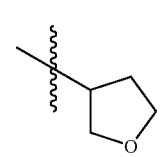
xiv
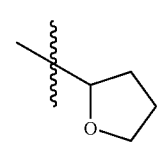
xv
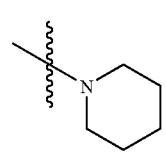
xvi
TABLE 1-continued
Ring B Moieties
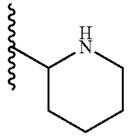
xvii
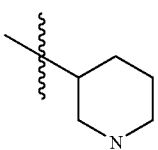
xviii
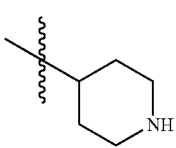
xix
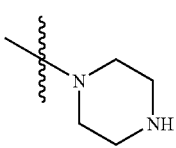
xx
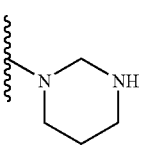
xxi
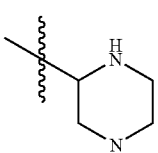
xxii
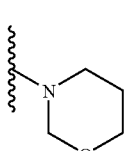
xxiii
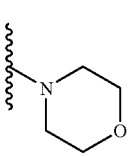
xxiv

TABLE 1-continued

Ring B Moieties xxv xxvi xxvii xxviii xxix xxx xxxi wherein each Ring B moiety depicted above in Table 1 is substituted with $QR^2$ and $(R^3)_p$.

Other embodiments contemplated by the present invention relate to compounds of formula I wherein any Ring B moiety depicted above is combined with any of the Ring A moieties depicted in formulae I-a, I-b, I-c, and I-d.

According to one embodiment, the present invention relates to a compound of formula I wherein Ring B is ring ii as depicted in Table 1 supra.

According to another embodiment, the present invention relates to a compound of formula I wherein Ring B is ring viii as depicted in Table 1 supra.

According to another embodiment, the present invention relates to a compound of formula I wherein Ring B is ring xxvii as depicted in Table 1 supra.

According to another embodiment, the present invention relates to a compound of formula I wherein Ring B is ring xxxi as depicted in Table 1 supra.

Another embodiment of this invention relates to a compound of formula II:

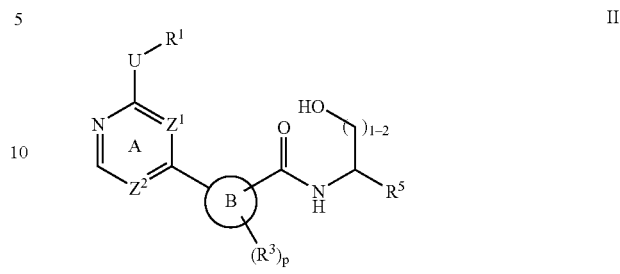

II or a pharmaceutically acceptable salt thereof, wherein:

Ring B is a 4–7 membered saturated ring having 0–3 heteroatoms independently selected from nitrogen, oxygen, or sulfur;

$Z^1$ is nitrogen or $CR^x$;

$R^x$ is selected from R, halogen, CN, $NO_2$, OR, SR, $N(R)_2$, C(O)R, or $CO_2R$, or:

$R^x$ and $U-R^1$ are taken together to form an optionally substituted 5–7 membered saturated, partially unsaturated, or fully unsaturated ring having 0–2 heteroatoms independently selected from nitrogen, oxygen, or sulfur;

$Z^2$ is nitrogen or $C-T_{(m)}R^y$;

T is selected from a saturated or unsaturated $C_{1-6}$ alkylidene chain wherein:

up to two methylene units of the chain are optionally and independently replaced by —C(O)—, —C(O)C(O)—, —C(O)NR—, —C(O)NRNR—, —$CO_2$—, —OC(O)—, —$NRCO_2$—, —O—, —NRC(O)NR—, —OC(O)NR—, —NRNR—, —NRC(O)—, —S—, —SO—, —$SO_2$—, —NR—, —$SO_2$NR—, or —$NRSO_2$—;

m is zero or one;

each R is independently selected from hydrogen or an optionally substituted $C_{1-6}$ aliphatic group, or:

two R on the same nitrogen are taken together with the nitrogen to form a 5–8 membered heterocyclyl or heteroaryl ring having 1–3 heteroatoms independently selected from nitrogen, oxygen, or sulfur;

$R^y$ is selected from R or Ar;

each Ar is an optionally substituted ring selected from a 6–10 membered aryl ring, a 5–10 membered heteroaryl ring having 1–4 heteroatoms independently selected from nitrogen, oxygen, or sulfur, or a 3–10 membered heterocyclyl ring having 1–4 heteroatoms independently selected from nitrogen, oxygen, or sulfur;

$R^1$ is selected from CN, R, Ar, —$(CH_2)_yCH(R^4)R^5$, or —$(CH_2)_yCH(R^4)CH(R^5)_2$;

each y is independently 0–6;

U is selected from a valence bond, —O—, —S—, —N(R)—, or a $C_{1-6}$ alkylidene chain wherein up to two methylene units of U are optionally and independently replaced by —O—, —S—, —SO—, —$SO_2$—, —N(R)$SO_2$—, —$SO_2$N(R)—, —N(R)—, —CO—, —$CO_2$—, —N(R)CO—, —N(R)C(O)O—, —N(R)CON(R)—, —N(R)$SO_2$N(R)—, —N(R)N(R)—, —C(O)N(R)—, or —OC(O)N(R)—;

y is 0–6;

$R^3$ is selected from oxo, R, F, Cl, $N(R)_2$, OR, SR, NRC(O)R, $NRC(O)N(R)_2$, $C(O)N(R)_2$, $SO_2R$, $NRSO_2R$, C(O)R, CN, $SO_2N(R)_2$, N(R)O, ON(R), or N(R)N(R);

p is 0–4;

$R^4$ is selected from R, $(CH_2)_wOR$, $(CH_2)_wN(R)_2$, or $(CH_2)_wSR$;

w is 0–4; and each $R^5$ is independently selected from optionally substituted $C_{1-6}$ aliphatic, Ar, $(CH_2)_wOR$, $CO_2R$, $(CH_2)_wN(R)_2$, N(Ar)(R), $(CH_2)_wSR$, NRC(O)R, NRC(O)N(R)$_2$, C(O)N(R)$_2$, SO$_2$R, NRSO$_2$R, C(O)R, CN, or SO$_2$N(R)$_2$.

The present invention relates to a compound of formula II, wherein Ring A is pyridinyl, pyrimidinyl, or triazinyl. Accordingly, the present invention relates to the following compounds of formulae II-a, II-b, II-c, and II-d:

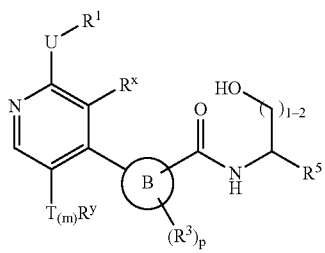

II-a

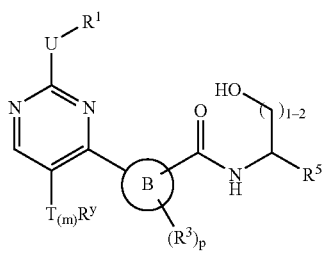

II-b

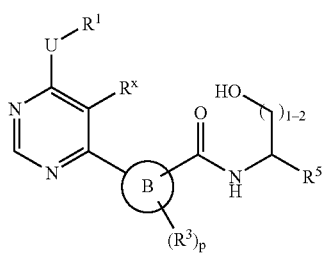

II-c

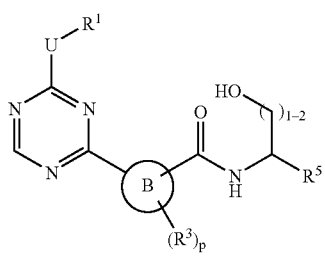

II-d

According to one embodiment, the present invention relates to a compound of formula II wherein Ring B is a 4–7 membered saturated ring having 1–2 nitrogens.

According to another embodiment, the present invention relates to a compound of formula II wherein Ring B is a 4–7 membered saturated ring having 1–2 oxygens.

Yet another embodiment of the present invention relates to a compound of formula II wherein Ring B is a 5–6 membered saturated ring having one oxygen and one nitrogen.

According to another embodiment, the present invention relates to a compound of formula II wherein Ring B is a 4–7 membered saturated ring having zero heteroatoms.

Another aspect of the present invention relates to a compound of formula II wherein Ring B is selected from the Ring B moieties set forth in Table 1 supra.

According to one embodiment, the present invention relates to a compound of formula II wherein Ring B is ring ii as depicted in Table 1 supra.

According to another embodiment, the present invention relates to a compound of formula II wherein Ring B is ring viii as depicted in Table 1 supra.

According to another embodiment, the present invention relates to a compound of formula II wherein Ring B is ring xxvii as depicted in Table 1 supra.

According to another embodiment, the present invention relates to a compound of formula II wherein Ring B is ring xxxi as depicted in Table 1 supra.

Another embodiment of this invention relates to a compound of formula III:

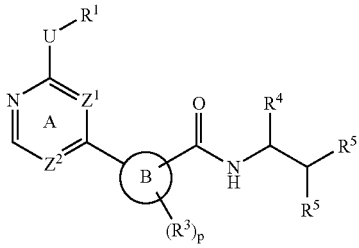

III or a pharmaceutically acceptable salt thereof, wherein:

Ring B is a 4–7 membered saturated ring having 0–3 heteroatoms independently selected from nitrogen, oxygen, or sulfur;

$Z^1$ is nitrogen or CR$^x$;

$R^x$ is selected from R, halogen, CN, NO$_2$, OR, SR, N(R)$_2$, C(O)R, or CO$_2$R, or:

R$^x$ and U-R$^1$ are taken together to form an optionally substituted 5–7 membered saturated, partially unsaturated, or fully unsaturated ring having 0–2 heteroatoms independently selected from nitrogen, oxygen, or sulfur;

$Z^2$ is nitrogen or C-T$_{(m)}$R$^y$;

T is selected from a saturated or unsaturated $C_{1-6}$ alkylidene chain wherein:

up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—;

m is zero or one;

each R is independently selected from hydrogen or an optionally substituted $C_{1-6}$ aliphatic group, or:

two R on the same nitrogen are taken together with the nitrogen to form a 5–8 membered heterocyclyl or heteroaryl ring having 1–3 heteroatoms independently selected from nitrogen, oxygen, or sulfur;

R$^y$ is selected from R or Ar;

each Ar is an optionally substituted ring selected from a 6–10 membered aryl ring, a 5–10 membered heteroaryl ring having 1–4 heteroatoms independently selected from nitrogen, oxygen, or sulfur, or a 3–10 membered heterocyclyl ring having 1–4 heteroatoms independently selected from nitrogen, oxygen, or sulfur;

$R^1$ is selected from CN, R, Ar, —(CH$_2$)$_y$CH(R$^4$)R$^5$, or —(CH$_2$)$_y$CH(R$^4$)CH(R$^5$)$_2$;

each y is independently 0–6;

U is selected from a valence bond, —O—, —S—, —N(R)—, or a C$_{1-6}$ alkylidene chain wherein up to two methylene units of U are optionally and independently replaced by —O—, —S—, —SO—, —SO$_2$—, —N(R)SO$_2$—, —SO$_2$N(R)—, —N(R)—, —CO—, —CO$_2$—, —N(R)CO—, —N(R)C(O)O—, —N(R)CON(R)—, —N(R)SO$_2$N(R)—, —N(R)N(R)—, —C(O)N(R)—, or —OC(O)N(R)—;

y is 0–6;

$R^3$ is selected from oxo, R, F, Cl, N(R)$_2$, OR, SR, NRC(O)R, NRC(O)N(R)$_2$, C(O)N(R)$_2$, SO$_2$R, NRSO$_2$R, C(O)R, CN, SO$_2$N(R)$_2$, N(R)O, ON(R), or N(R)N(R);

p is 0–4;

$R^4$ is selected from R, (CH$_2$)$_w$OR, (CH$_2$)$_w$N(R)$_2$, or (CH$_2$)$_w$SR;

w is 0–4; and each $R^5$ is independently selected from optionally substituted C$_{1-6}$ aliphatic, Ar, (CH$_2$)$_w$OR, CO$_2$R, (CH$_2$)$_w$N(R)$_2$, N(Ar)(R), (CH$_2$)$_w$SR, NRC(O)R, NRC(O)N(R)$_2$, C(O)N(R)$_2$, SO$_2$R, NRSO$_2$R, C(O)R, CN, or SO$_2$N(R)$_2$.

The present invention relates to a compound of formula III, wherein Ring A is pyridinyl, pyrimidinyl, or triazinyl. Accordingly, the present invention relates to the following compounds of formulae III-a, III-b, III-c, and III-d:

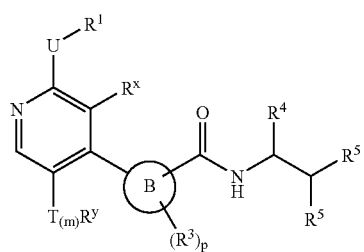

III-a

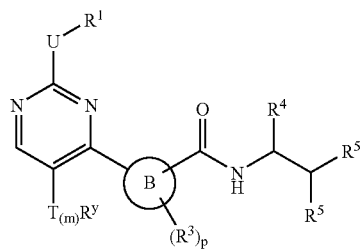

III-b

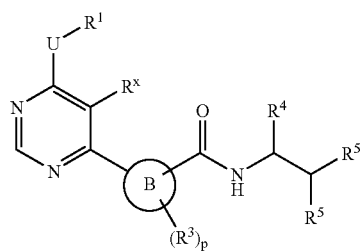

III-c

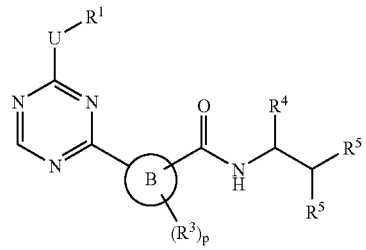

III-d

According to one embodiment, the present invention relates to a compound of formula III wherein Ring B is a 4–7 membered saturated ring having 1–2 nitrogens.

According to another embodiment, the present invention relates to a compound of formula III wherein Ring B is a 4–7 membered saturated ring having 1–2 oxygens.

Yet another embodiment of the present invention relates to a compound of formula III wherein Ring B is a 5–6 membered saturated ring having one oxygen and one nitrogen.

According to another embodiment, the present invention relates to a compound of formula III wherein Ring B is a 4–7 membered saturated ring having zero heteroatoms.

Another aspect of the present invention relates to a compound of formula III wherein Ring B is selected from the Ring B moieties set forth in Table 1 supra.

According to one embodiment, the present invention relates to a compound of formula III wherein Ring B is ring ii as depicted in Table 1 supra.

According to another embodiment, the present invention relates to a compound of formula III wherein Ring B is ring viii as depicted in Table 1 supra.

According to another embodiment, the present invention relates to a compound of formula III wherein Ring B is ring xxvii as depicted in Table 1 supra.

According to another embodiment, the present invention relates to a compound of formula III wherein Ring B is ring xxxi as depicted in Table 1 supra.

Another embodiment of this invention relates to a compound of formula IV:

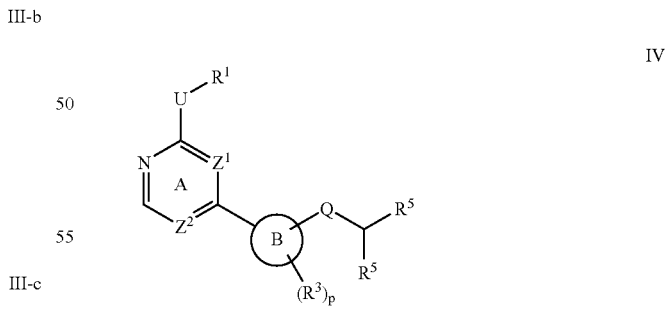

IV or a pharmaceutically acceptable salt thereof, wherein:

Ring B is a 4–7 membered saturated ring having 0–3 heteroatoms independently selected from nitrogen, oxygen, or sulfur;

$Z^1$ is nitrogen or CR$^x$;

$R^x$ is R, halogen, CN, NO$_2$, OR, SR, N(R)$_2$, C(O)R, or CO$_2$R, or:

R$^x$ and U-R$^1$ are taken together to form an optionally substituted 5–7 membered saturated, partially unsaturated, or fully unsaturated ring having 0–2 heteroatoms independently selected from nitrogen, oxygen, or sulfur;

Z$^2$ is nitrogen or C-T$_{(m)}$R$^y$;

Q is NRC(O), C(O)NR, NRSO$_2$, or SO$_2$NR;

T is a saturated or unsaturated C$_{1-6}$ alkylidene chain wherein:

up to two methylene units of the chain are optionally and independently replaced by —C(O)—, —C(O)C(O)—, —C(O)NR—, —C(O)NRNR—, —CO$_2$—, —OC(O)—, —NRCO$_2$—, —O—, —NRC(O)NR—, —OC(O)NR—, —NRNR—, —NRC(O)—, —S—, —SO—, —SO$_2$—, —NR—, —SO2NR—, or —NRS$_2$—;

m is zero or one;

each R is independently selected from hydrogen or an optionally substituted C$_{1-6}$ aliphatic group, or:

two R on the same nitrogen are taken together with the nitrogen to form a 5–8 membered heterocyclyl or heteroaryl ring having 1–3 heteroatoms independently selected from nitrogen, oxygen, or sulfur;

R$^y$ is selected from R or Ar;

each Ar is an optionally substituted ring selected from a 6–10 membered aryl ring, a 5–10 membered heteroaryl ring having 1–4 heteroatoms independently selected from nitrogen, oxygen, or sulfur, or a 3–10 membered heterocyclyl ring having 1–4 heteroatoms independently selected from nitrogen, oxygen, or sulfur;

R$^1$ is selected from CN, R, Ar, —(CH$_2$)$_y$CH(R$^4$)R$^5$, or —(CH$_2$)$_y$CH(R$^4$)CH(R$^5$)$_2$;

each y is independently 0–6;

U is selected from a valence bond, —O—, —S—, —N(R)—, or a C$_{1-6}$ alkylidene chain wherein up to two methylene units of U are optionally and independently replaced by —O—, —S—, —SO—, —SO$_2$—, —N(R)SO$_2$—, —SO$_2$N(R)—, —N(R)—, —CO—, —CO$_2$—, —N(R)CO—, —N(R)C(O)O—, —N(R)CON(R)—, —N(R)SO$_2$N(R)—, —N(R)N(R)—, —C(O)N(R)—, or —OC(O)N(R)—;

y is 0–6;

R$^3$ is selected from oxo, R, F, Cl, N(R)$_2$, OR, SR, NRC(O)R, NRC(O)N(R)$_2$, C(O)N(R)$_2$, SO$_2$R, NRSO$_2$R, C(O)R, CN, SO$_2$N(R)$_2$, N(R)O, ON(R), or N(R)N(R);

p is 0–4;

R$^4$ is selected from R, (CH$_2$)$_w$OR, (CH$_2$)$_w$N(R)$_2$, or (CH$_2$)$_w$SR;

w is 0–4; and each R$^5$ is independently selected from optionally substituted C$_{1-6}$ aliphatic, Ar, (CH$_2$)$_w$OR, CO$_2$R, (CH$_2$)$_w$N(R)$_2$, N(Ar)(R), (CH$_2$)$_w$SR, NRC(O)R, NRC(O)N(R)$_2$, C(O)N(R)$_2$, SO$_2$R, NRSO$_2$R, C(O)R, CN, or SO$_2$N(R)$_2$.

The present invention relates to a compound of formula IV, wherein Ring A is pyridinyl, pyrimidinyl, or triazinyl. Accordingly, the present invention relates to the following compounds of formulae IV-a, IV-b, IV-c, and IV-d:

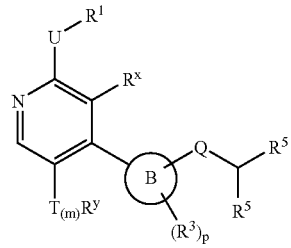

IV-a

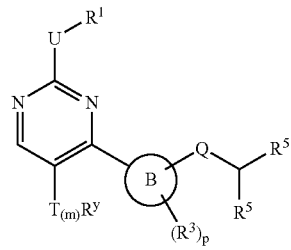

IV-b

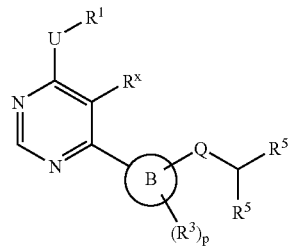

IV-c

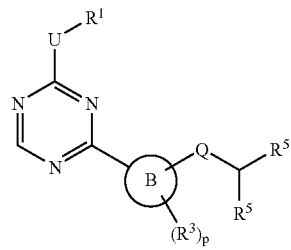

IV-d

According to one embodiment, the present invention relates to a compound of formula IV wherein Ring B is a 4–7 membered saturated ring having 1–2 nitrogens.

According to another embodiment, the present invention relates to a compound of formula IV wherein Ring B is a 4–7 membered saturated ring having 1–2 oxygens.

Yet another embodiment of the present invention relates to a compound of formula IV wherein Ring B is a 5–6 membered saturated ring having one oxygen and one nitrogen.

According to another embodiment, the present invention relates to a compound of formula IV wherein Ring B is a 4–7 membered saturated ring having zero heteroatoms.

Another aspect of the present invention relates to a compound of formula IV wherein Ring B is selected from the Ring B moieties set forth in Table 1 supra.

According to one embodiment, the present invention relates to a compound of formula IV wherein Ring B is ring ii as depicted in Table 1 supra.

According to another embodiment, the present invention relates to a compound of formula IV wherein Ring B is ring viii as depicted in Table 1 supra.

According to another embodiment, the present invention relates to a compound of formula IV wherein Ring B is ring xxvii as depicted in Table 1 supra.

According to another embodiment, the present invention relates to a compound of formula IV wherein Ring B is ring xxxi as depicted in Table 1 supra.

Exemplary structures of compounds of formula I are set forth in Table 2 below.

TABLE 2

Examplary Compounds of Formula I

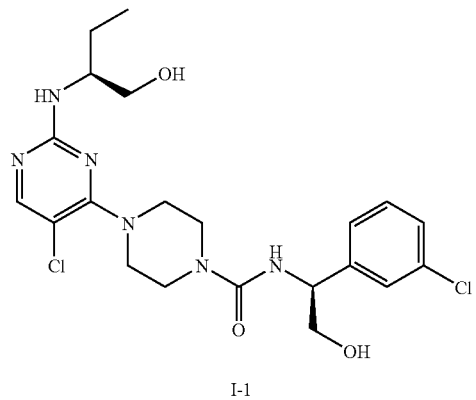

I-1

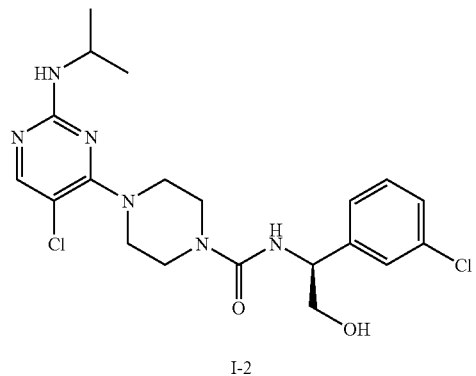

I-2

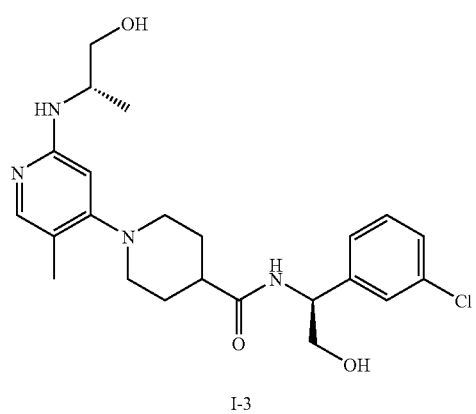

I-3

TABLE 2-continued

Examplary Compounds of Formula I

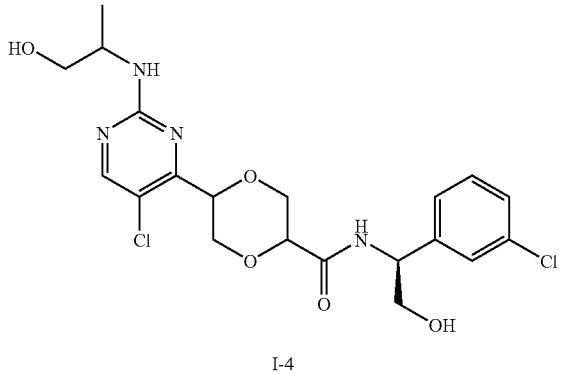

I-4

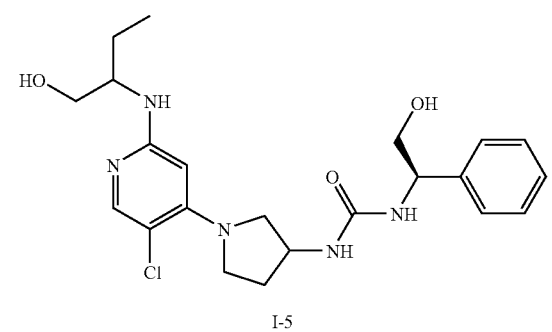

I-5

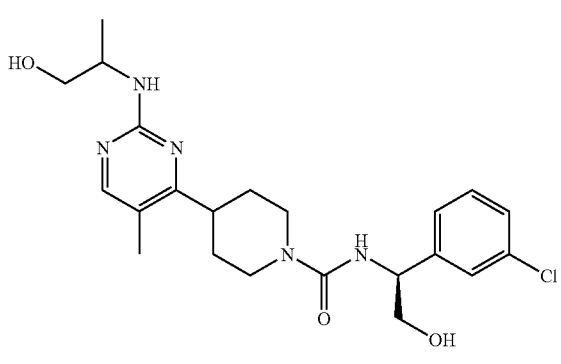

I-6

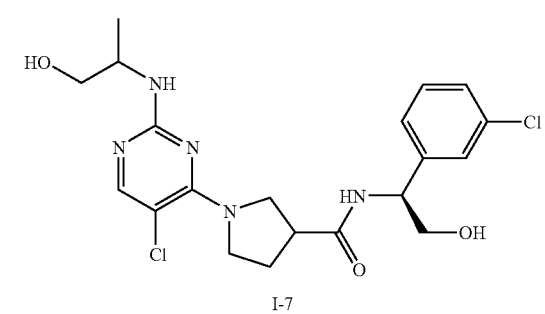

I-7

TABLE 2-continued

Examplary Compounds of Formula I

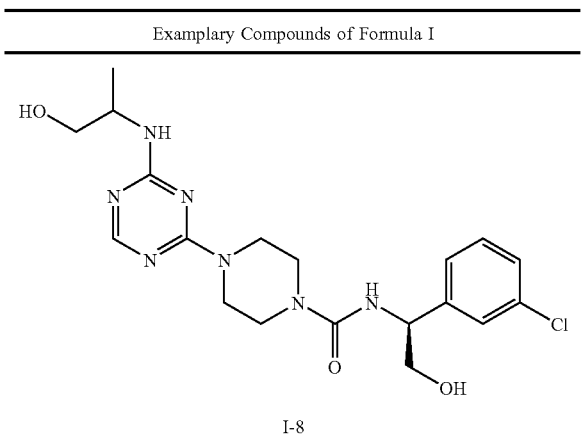

I-8

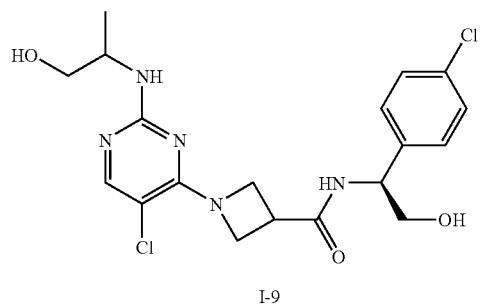

I-9

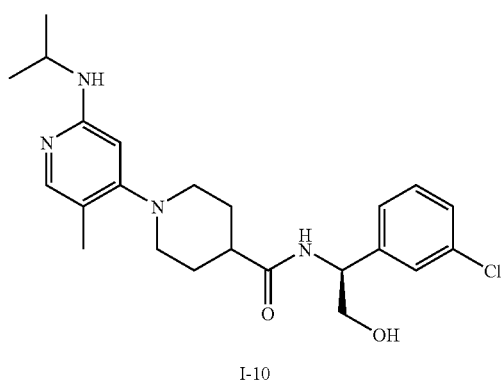

I-10

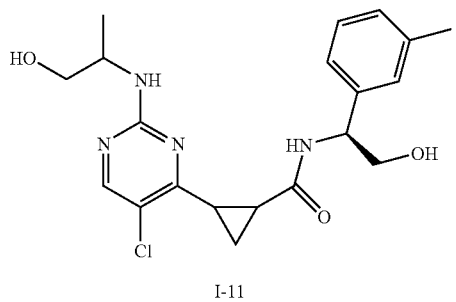

I-11

TABLE 2-continued

Examplary Compounds of Formula I

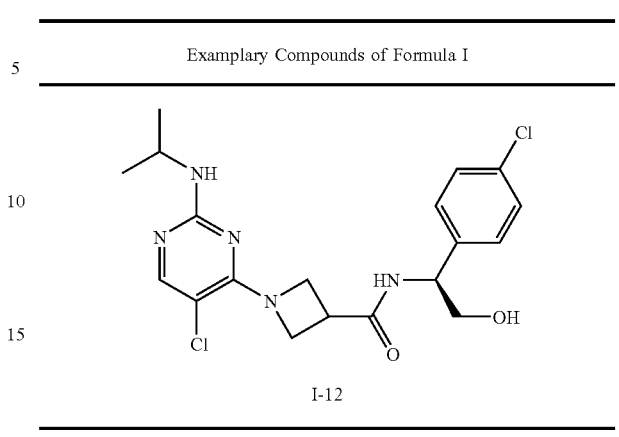

I-12

4. General Methods of Providing the Present Compounds:

The present compounds may be prepared in general by methods known to those skilled in the art for analogous compounds, as illustrated by the general Schemes I, II, and III and the synthetic examples set forth below.

Scheme I

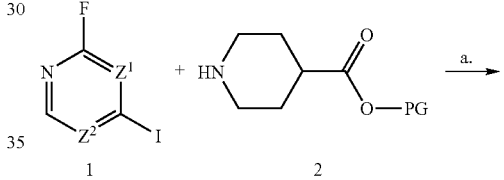

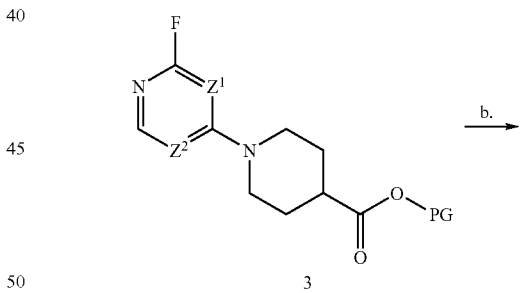

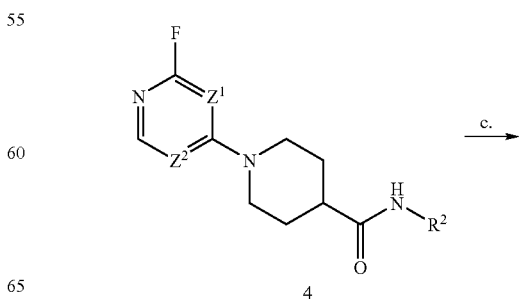

-continued

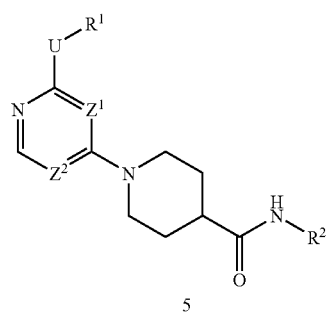
5

Reagents and conditions:
a. Pd(OAc)$_2$, 1,3-bis(diphenylphosphino)propane, DMF, Cs$_2$CO$_3$, 160° C. microwave;
b. (i) carboxylate deprotection, (ii) R$^2$—NH$_2$, diisopropylethylamine, EDCI, DIEA;
c. R$^1$—UH, DMSO, 160° C.

Scheme I above depicts a general method for preparing compounds of the present invention wherein Ring B is piperadinyl, ring xvi. The iodo starting material 1 is treated with carboxyl protected piperidine-4-carboxylic acid in the presence of Pd(OAc)$_2$ and 1,3-bis(diphenylphosphino)propane to form compound 3. One of ordinary skill in the art would recognize that various carboxyl protecting groups may be used and that the method for removal of said protecting group depends on the actual protecting group utilized. Such carboxyl protecting groups are well known in the art and include those recited by "Protective Groups in Organic Synthesis" Third Ed. Greene, T. W. and Wuts, P. G., Eds., John Wiley & Sons, New York: 1999, the entire contents of which are hereby incorporated by reference.

The carboxyl protecting group of compound 3 is removed and the resulting carboxylic acid is coupled with an amine of formula R$^2$—NH$_2$ to form intermediate 4. One of ordinary skill in the art would recognize that a variety of compounds may be coupled to the carboxylic moiety of deprotected compound 3 to form compounds of the present invention wherein Q is selected from other groups in addition to the amide depicted above. For example, said carboxylic acid can be coupled with an alcohol of formula R$^2$—OH to form compounds of the present invention wherein Q is —C(O)O—. Alternatively, said carboxylic acid may be treated with chlorinating reagents known in the art (e.g., oxalyl chloride or PCl$_5$) to form the acyl chloride derivative. One of ordinary skill in the art would recognize that this acyl chloride derivative may be used to prepare a variety of compounds of the present invention including those wherein Q is —C(O)—.

The fluoro group of compound 4 is then displaced by a compound of formula R$^1$—UH to form compounds of the present invention wherein Ring B is piperadinyl ring xvi. One of ordinary skill in the art would recognize that numerous compounds of the present invention are prepared using the above general method.

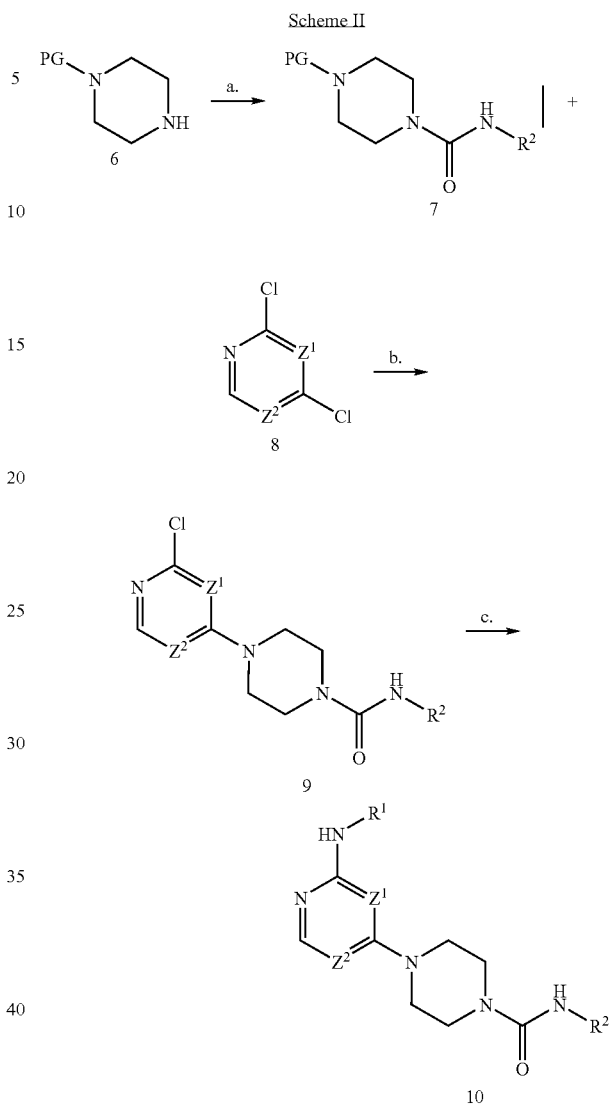

Conditions:
a. triphosgene, CH$_2$Cl$_2$, -78° C., R$^2$—NH$_2$
b. (i) amine deprotection, (ii) DMF, DIEA, 80° C.;
c. R$^1$—NH$_2$ EtOH, 70° C.

Scheme II above depicts a general method for preparing compounds of the present invention wherein Ring B is piperazinyl, ring xx. The amino-protected piperazinyl starting material 6 is treated with triphosgene then an amine of formula R$^2$—NH$_2$ to form intermediate 7. One of ordinary skill in the art would recognize that various amine protecting groups may be used and that the method for removal of said protecting group depends on the actual protecting group utilized. Such amine protecting groups are well known in the art and include those recited by "Protective Groups in Organic Synthesis" Third Ed. Greene, T. W. and Wuts, P. G., Eds., John Wiley & Sons, New York: 1999.

The amine protecting group of compound 7 is removed and the resulting compound treated with the dichloro compound 8 to form monochloro compound 9. The chloro moiety of compound 9 is displaced with an amine of formula R$^1$—NH$_2$ to form compound 10. One of ordinary skill in the art would recognize that numerous compounds of the present invention are prepared using the above general method.

Scheme III

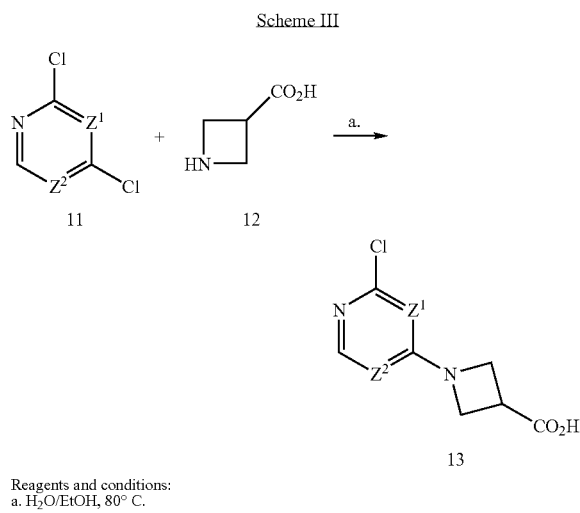

Reagents and conditions:
a. H$_2$O/EtOH, 80° C.

Scheme III above depicts a general method for preparing compounds of the present invention wherein Ring B is azetidinyl, ring xxvii. The dichloro starting material, 11, is treated with azetidine-3-carboxylic acid to form compound 13. Compound 13 is then used to prepare compounds of the present invention using methods described above for Schemes I and II and by methods known to one of ordinary skill in the art. One of ordinary skill in the art would recognize that numerous compounds of the present invention are prepared using the above general method.

5. Uses, Formulation and Administration Pharmaceutically Acceptable Compositions The compounds and compositions described herein are generally useful for the inhibition of protein kinase activity of one or more enzymes. Further information relating to kinase structure, function and their role in disease or disease symptoms is available at the Protein Kinase Resource website.

Examples of kinases that are inhibited by the compounds and compositions described herein and against which the methods described herein are useful include, but are not limited to, ERK1, ERK2, GSK3, ROCK, JAK1, JAK2, JAK3, CDK1, CDK2, and/or CDK5, and all subtypes of these kinases. The compounds and compositions of the invention are therefore also particularly suited for the treatment of diseases and disease symptoms that involve one or more of the aforementioned kinases.

In one particular embodiment, the compounds and compositions of the invention are inhibitors of one or more of ERK2, GSK3, ROCK, JAK3, and/or CDK2, and thus the compounds and compositions are particularly useful for treating or lessening the severity of disease or disease symptoms associated with ERK2, GSK3, ROCK, JAK3, and/or CDK2.

The activity of a compound utilized in this invention as an inhibitor of ERK2, GSK3, ROCK, JAK3, and/or CDK2, may be assayed in vitro, in vivo or in a cell line. In vitro assays include assays that determine inhibition of either the phosphorylation activity or ATPase activity of activated ERK2, GSK3, ROCK, JAK3, and/or CDK2. Alternate in vitro assays quantitate the ability of the inhibitor to bind to ERK2, GSK3, ROCK, JAK3, and/or CDK2. Inhibitor binding may be measured by radiolabelling the inhibitor prior to binding, isolating the inhibitor/ERK2, inhibitor/GSK3, inhibitor/ROCK, inhibitor/JAK3, or inhibitor/CDK2, complex and determining the amount of radiolabel bound. Alternatively, inhibitor binding may be determined by running a competition experiment where new inhibitors are incubated with ERK2, GSK3, ROCK, JAK3, and/or CDK2 bound to known radioligands. Detailed conditions for assaying a compound utilized in this invention as an inhibitor of ERK2, GSK3, ROCK, JAK3, and/or CDK2 kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly ERK2, GSK3, ROCK, JAK3, and/or CDK2 kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in ERK2, GSK3, ROCK, JAK3, and/or CDK2 activity between a sample comprising said composition and a ERK2, GSK3, ROCK, JAK3, and/or CDK2 kinase and an equivalent sample comprising ERK2, GSK3, ROCK, JAK3, and/or CDK2 kinase in the absence of said composition.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ERK2, GSK3, ROCK, JAK3, and/or CDK2.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting ERK2, GSK3, ROCK, JAK3, and/or CDK2 kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from ERK2, GSK3, ROCK, JAK3, and/or CDK2 kinase, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting ERK2, GSK3, ROCK, JAK3, and/or CDK2 kinase activity in a patient comprising the step of administering to said patient a compound of the present invention, or a composition comprising said compound.

According to another embodiment, the invention provides a method for treating or lessening the severity of an ERK2-mediated disease or condition in a patient comprising the step of administering to said patient a composition according to the present invention.

The term "ERK-mediated disease" or "condition", as used herein means any disease or other deleterious condition in which ERK is known to play a role. Accordingly, another embodiment of the present invention relates to treating or lessening the severity of one or more diseases in which ERK is known to play a role. Specifically, the present invention relates to a method of treating or lessening the severity of a disease or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein said method comprises administering to a patient in need thereof a composition according to the present invention.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another embodiment relates to a method of treating melanoma, breast cancer, colon cancer, or pancreatic cancer in a patient in need thereof.

The term "GSK3-mediated disease" or "condition", as used herein means any disease or other deleterious condition in which GSK3 is known to play a role. Accordingly, another embodiment of the present invention relates to treating or lessening the severity of one or more diseases in which GSK3 is known to play a role. Specifically, the present invention relates to a method of treating or lessening the severity of a disease or condition selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease wherein said method comprises administering to a patient in need thereof a composition according to the present invention.

According to another embodiment, the present invention relates to a method for treating or lessening the severity of a disease or condition selected from allergy, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), an injury due to head trauma, schizophrenia, anxiety, bipolar disorder, tauopothy, a spinal cord or peripheral nerve injury, myocardial infarction, cardiomyocyte hypertrophy, glaucoma, attention deficit disorder (ADD), depression, a sleep disorder, reperfusion/ischemia, stroke, an angiogenic disorder, or baldness, wherein said method comprises administering to a patient in need thereof a compound of the present invention or composition thereof.

According to a preferred embodiment, the method of the present invention relates to treating or lessening the severity of stroke.

According to another preferred embodiment, the method of the present invention relates to treating or lessening the severity of a neurodegenerative or neurological disorder.

Another aspect of the present invention relates to a method of decreasing sperm motility in a male patient comprising administering to said patient a compound of the present invention or composition thereof.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Accordingly, another embodiment of the present invention relates to treating or lessening the severity of one or more diseases in which ROCK is known to play a role. Specifically, the present invention relates to a method of treating or lessening the severity of a disease or condition selected from hypertension, angina pectoris, cerebrovascular contraction, asthma, peripheral circulation disorder, premature birth, cancer, arteriosclerosis, spasm, retinopathy, inflammatory disorders, autoimmune disorders, AIDS, and osteoporosis, wherein said method comprises administering to a patient in need thereof a composition according to the present invention.

According to another embodiment, the invention provides a method for treating or lessening the severity of a JAK-mediated disease or condition in a patient comprising the step of administering to said patient a composition according to the present invention.

The term "JAK-mediated disease", as used herein means any disease or other deleterious condition in which a JAK family kinase is known to play a role. Accordingly, another embodiment of the present invention relates to treating or lessening the severity of one or more diseases in which JAK is known to play a role. Specifically, the present invention relates to a method of treating or lessening the severity of a disease or condition selected from immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas, wherein said method comprises administering to a patient in need thereof a composition according to the present invention.

The compounds of this invention are also useful as inhibitors of CDK2 kinase. Accordingly, these compounds are useful for treating or lessening the severity of CDK2-mediated diseases or conditions.

The term "CDK2-mediated disease", as used herein means any disease or other deleterious condition in which CDK2 is known to play a role. Accordingly, these compounds are useful for treating diseases or conditions that are known to be affected by the activity of CDK2 kinase. Such diseases or conditions include viral infections, neurodegenerative disorders, and disorders associated with thymocyte apoptosis. Such diseases or conditions also include proliferative disorders resulting from the deregulation of the cell cycle, especially of the progression from $G_1$ to S phase.

According to another embodiment, the present invention relates to a method of treating or lessening the severity of a cancer comprising the step of blocking the transition of cancer cells into their proliferative phase by inhibiting CDK2 with a compound of the present invention, or pharmaceutically acceptable composition thereof.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01–100 mg/kg body weight/day of a compound of formula I can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01–100 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

SYNTHETIC EXAMPLES

As used herein, the term "$R_t$" refers to the retention time, in minutes, obtained for the specified compound using the following HPLC method, unless indicated otherwise:

Column: YMC ODS AQ, 3×150 mm, C18, 5 mm
Gradient: 90% water/10% $CH_3CN$, 0.1% TFA to 0% water/100% $CH_3CN$, 0.1% TFA over 8 minutes
Wavelength: 214 nM
Flow rate: 1 mL/minute Unless otherwise indicated, each $^1H$ NMR was obtained at 500 MHz in $CDCl_3$.

Example 1

1-(2,5-Dichloropyrimidin-4-yl)-azetidine-3-carboxylic acid: To a suspension of azetidine-3-carboxylic acid (56 mg, 0.55 mmol, 1 equiv.) in water (1 mL) and ethanol (0.3 mL), was added 2,4,6-trichloropyrimidine (101 mg, 0.55 mmol, 1 equivalent). The resulting mixture was heated at reflux at 99° C. for 1 hour. The reaction mixture was cooled down and the resulting precipitated solid was isolated by filtration to afford the title compound (66 mg, 49%). LC/MS: $R_t$=2.1 minutes; ES+247.9, ES-246.0.

Example 2

1-(2,5-dichloropyrimidin-4-yl)-azetidine-3-carboxylic acid [1-(3-chlorophenyl)-2-hydroxyethyl]-amide: 1-(2,5-Dichloropyrimidin-4-yl)-azetidine-3-carboxylic acid (66 mg, 0.27 mmol, 1 equivalent) was dissolved in DMF (1 mL) together with EDCI (103 mg, 0.53 mmol, 2 equivalents), HOBt (18 mg, 0.13 mmol, 0.5 equivalent) and (S)-(+)-3-chlorophenylglycinol (67.4 mg, 0.32 mmol, 1.2 equivalents). Triethylamine (121 mg, 0.32 mmol, 1.2 equivalents) was then added and the resulting mixture was stirred at room temperature for 1 hour then warmed to 90° C. for 10 minutes. The crude reaction mixture was diluted with ethyl acetate, washed with water, and the organic fraction dried over sodium sulfate. The resulting crude oil was purified by HPLC Gilson (acetonitrile/water/0.1% TFA), yielding the title compound as a white solid (44 mg, 41%). HPLC $R_t$=5.528 minutes.

Example 3

1-(5-chloro-2-(2-hydroxy-1-methylethylamino)-pyrimidin-4-yl)-azetidine-3-carboxylic acid [1-(3-chlorophenyl)-2-hydroxyethyl]-amide (I-9): 1-(2,5-dichloropyrimidin-4-yl)-azetidine-3-carboxylic acid [1-(3-chlorophenyl)-2-hydroxyethyl]-amide (16 mg, 0.04 mmol, 1 equiv.) was dissolved in 1-butanol (1 mL). (S)-2-Aminopropanol (0.02 mL, 0.2 mmol, 5 equiv.) was then added and the resulting mixture was microwave irradiated (185° C., 1200 sec, high absorption). The resulting crude mixture was purified first by HPLC Gilson (acetonitrile/water/0.1% TFA), followed by preparative-TLC on silica gel (DCM/MeOH from 95:5 to 90:10). The title compound was isolated as a white solid (3.9 mg, 21%). LC/MS: $R_t$=2.0 minutes; ES+454.0, ES-452.2. $^1H$ NMR (Acetone-$d_6$)δ 0.95 (t, 3H), 1.5 (m, 1H), 1.7 (m, 1H), 3.6 (m, 3H), 3.85 (m, 3H), 4.4 (m, 4H), 5.1 (t, 1H), 5.6 (bs, 1H), 7.25 (m, 1H), 7.3 (m ,2H), 7.4 (s, 1H), 7.7 (overlapped two s, 2H).

Example 4

2-Fluoro-5-methyl-4-(4-ethoxycarbonyl-piperdinyl)pyridine: Palladium acetate (0.04 mmol, 10 mg) was stirred with 1,3-bis(diphenylphosphino)propane (18 mg, 0.04 mmol) in DMF (0.5 mL) for 10 minutes. A mixture of 2-fluoro-4-iodo-5-methyl pyridine (0.42 mmol, 100 mg), ethyl-1-piperidinecarboxylate (0.5 mmol, 0.08 mL) and cesium carbonate (275 mg, 2 equiv) in DMF (1.5 mL) was then added, stirred vigorously, and heated in the microwave to 160° C. for 10 minutes. The resulting black mixture was poured onto a silica gel column and purified by flash chromatography (ethyl acetate/hexanes gradient) to afford 61 mg of the title compound as a yellow oil (54%). $R_t$=6.70 minutes; MS FIA 267.1 (M+1).

Example 5

2'-Fluoro-3,4,5,6-tetrahydro-2H-[1,4']bipyridinyl-4-carboxylic acid [1-(3-chloro-phenyl)-2-hydroxy-ethyl]-amide: 2-Fluoro-5-methyl-4-(4-ethoxycarbonyl-piperdinyl)pyridine (60 mg, 0.23 mmol) was stirred with THF (2 mL), water (1 mL) and lithium hydroxide (50 mg, 10 eq). The mixture stirred 18 hours at ambient temperature and was then diluted with ethyl acetate and washed with potassium hydrogen sulfate (5% aqueous). The organic layer was dried ($MgSO_4$) and concentrated in vacuo to afford the acid intermediate, $R_t$=4.43 minutes and MS FIA ES+239. 1. This acid was combined with (S)-(+)-3-chloro-phenylgylcinolHCL salt (47 mg. 0.23 mmol), 1–3(dimethylaminopropyl)-3-ethylcarbodiimide hydrochloride (48 mg, 0.25 mmol), and diisopropylethyl amine (0.2 mL) in methylene chloride and the resulting mixture stirred overnight. The reaction mixture was concentrated in vacuo and the residue purification by preparative HPLC (Gilson: Column=CombiHT SB-C189 5 μM 21.2 mm ×100 mm, eluent=0.1% TFA MeCN/$H_2O$ gradient) to afford the title compounds as a white solid (10 mg) $R_t$=4.28 minutes; MS FIA 392.1 (M+1); $^1H$ NMR consistent with structure.

Example 6

2'-(2-Hydroxy-1-methyl-ethylamino)-3,4,5,6-tetrahydro-2H-[1,4']bipyridinyl-4-carboxylic acid [1-(3-chloro-phenyl)-2-hydroxy-ethyl]-amide (I-3): The 2'-fluoro-3,4,5, 6-tetrahydro-2H-[1,4']bipyridinyl-4-carboxylic acid [1 -(3-chloro-phenyl)-2-hydroxy-ethyl]-amide compound (10 mg, 0.026 mmol) was combined with (S)-2-amino-propanol (0.2 mL) in DMSO and heated in an oil bath to 160° C. for 18 hours. The crude mixture was pipetted onto a preparative TLC plate (1 mm silica) and the compound eluted with ethyl acetate. Isolation of the most UV active band afforded 2.6 mg of the title product as a colorless oil. $R_t$=4.40 minutes, LCMS 447.3 (M=1), $^1H$ NMR δ 7.66 (s, 1H) 7.32–7.20 (m, 4H) 6.34 (NH) 5.94 (s, 1H) 5.07–5.06 (m, 1H) 4.17 (m, 1H) 3.90 (m, 1H) 3.62 (m, 2H) 3.36 (m, 2H) 2.85 (m, 1H) 2.63 (m, 2H) 2.33 (m, 1H) 2.08 (s, 3H) 1.94 (m, 4H) 1.19 (d, 3H).

Example 7

4-[1-(3-Chloro-phenyl)-2-hydroxy-ethylcarbamoyl]-piperazine-1-carboxylic acid tert-butyl ester: Triphosgene (264 mg, 0.89 mmol) was dissolved in methylene chloride (20 mL) and the mixture cooled to −78° C. under nitrogen atmosphere. A mixture of t-butoxycarbonyl-piperazine (500 mg, 2.4 mmol) and diisopropylethylamine (2 mL) in $CH_2Cl_2$ was added dropwise to the cold stirring solution over 30 minutes. When the addition was complete, a mixture of (S)-(+)-3-chlorophenylglycinol (500 mg, 2.4 mmol) and DIEA (2 mL) in $CH_2CL_2$ (5 mL) was added. The reaction warmed to ambient temperature and concentrated in vacuo. The resulting residue was purified by preparative HPLC (Gilson: Column=CombiHT SB-C189 5 μM 21.2 mm×100 mm, eluent=0.1% TFA MeCN/$H_2O$ gradient) to afford the desired compound as a yellow oil (134 mg) $R_t$=6.72 minutes.

Example 8

1-(2,5-Dichloro-pyrimidin-4-yl)-piperidine-4-carboxylic acid [1-(3-chloro-phenyl)-2-hydroxy-ethyl]-amide: 4-[1-(3-Chloro-phenyl)-2-hydroxy-ethylcarbamoyl]-piperazine-1-carboxylic acid tert-butyl ester was deprotected with 10% trifluoroacetic acid in methylene chloride by stirring overnight at ambient temperature. The reaction was concentrated in vacuo and the resulting TFA salt was dissolved in DMF (1 mL) and DIEA (0.25 mL). This mixture was heated with 2,4,5-trichloropyrimidine (52 mg. 0.28 mmol) at 80° C. for 18 hours. Purification by prep HPLC (Gilson: Column=CombiHT SB-C189 5 μM 21.2 mm×100 mm, eluent=0.1% TFA MeCN/$H_2O$ gradient) afforded the title compound as a yellow oil (47 mg) $R_t$=5.97 minutes; MS FIA 429.9 (M+1).

Example 9

1-(5-Chloro-2-isopropylamino-pyrimidin-4-yl)-piperidine-4-carboxylic acid [1-(3-chloro-phenyl)-2-hydroxy-ethyl]-amide (I-2): The 1-(2,5-dichloro-pyrimidin-4-yl)-piperidine-4-carboxylic acid [1-(3-chloro-phenyl)-2-hydroxy-ethyl]-amide (60 mg, 0.14 mmol) compound was dissolved in absolute ethanol (1 mL) and isopropyl amine (0.2 mL). The mixture was heated in a sealed Teflon reaction vial at 70° C. overnight. The resulting mixture was filtered and purified by preparative HPLC (Gilson: Column=CombiHT SB-C189 5 μM 21.2 mm×100 mm, eluent=0.1% TFA MeCN/$H_2O$ gradient). Further purification by preparative TLC (1 mm silica; eluent ethyl acetate) afforded the title compound as a colorless oil (19.5 mg) $R_t$=4.82 minutes; LCMS 453.1 (M+1); $^1$H NMR δ 7.87 (s, 1H) 7.25 (m, 4H) 5.28 (NH) 4.95 (dd, J=5.9, 3.9 Hz, 1H) 4.81 (NH) 4.01 (m, 1H) 3.89 (dd, J=11.2, 3.9 Hz, 1H) 3.83 (dd, J=11.2, 5.9 Hz, 1H) 3.65 (m, 4H) 3.52 (m 4H) 2.1 (OH) 1.20 (d, J=6.5 Hz, 6H).

Example 10

1-[5-Chloro-2-(1-hydroxymethyl-propylamino)-pyrimidin-4-yl]-piperidine-4-carboxylic acid [1-(3-chloro-phenyl)-2-hydroxy-ethyl]-amide (I-1): 1-(2,5-Dichloro-pyrimidin-4-yl)-piperidine-4-carboxylic acid [1-(3-chloro-phenyl)-2-hydroxy-ethyl]-amide (20 mg, 0.05 mmol) was dissolved in absolute ethanol (1 mL) then (S)-2-amino-butanol (0.1 mL) was added. The mixture was heated in a sealed Teflon reaction vial at 80° C. overnight. The resulting mixture was purified by preparative TLC (1 mm silica; eluent ethyl acetate) to afford the title compound as a colorless oil (4 mg). LC/MS $R_t$=4.42 minutes; 483.0 (M+1); $^1$H NMR δ 7.88 (s, 1H) 7.26 (m, 4H) 5.21 (NH) 4.97 (m, 1H) 3.91 (dd, J=11.2, 3.8, 1H) 3.86 (dd, J=11.2, 5.8, 1H) 3.7 (m, 1H) 3.66 (m, 5H) 3.62 (m, 1H) 3.54 (m, 4H) 1.65 (m, 1H) 1.54 (m, 1H) 1.26 (OH) 0.99 (t, J=7.5, 3H).

Example 11

1-(5-Chloro-2-isopropylamino-pyrimidin-4-yl)-azetidine-3-carboxylic acid [1-(4-chloro-phenyl)-2-hydroxy-ethyl]-amide (I-12): (M+1) 454; (M−1) 452.2; $^1$H NMR (Acetone-d6) δ 0.95 (t, 3H), 1.5 (m, 1H), 1.7 (m, 1H), 3.6 (m, 3H), 3.85 (m, 3H), 4.4 (m, 4H), 5.1 (t, 1H), 5.6 (bs, 1H), 7.25 (m, 1H), 7.3 (m, 2H), 7.4 (s, 1H), 7.7 (overlapped 2 s, 2H).

Example 12

CDK-2 Inhibition Assay

Compounds were screened in the following manner for their ability to inhibit CDK-2 using a standard coupled enzyme assay (Fox et al (1998) *Protein Sci* 7, 2249).

To an assay stock buffer solution containing 0.1 M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 μM peptide (American Peptide, Sunnyvale, Calif.) was added a DMSO solution of a compound of the present invention to a final concentration of 30 μM. The resulting mixture was incubated at 30° C. for 10 minutes.

The reaction was initiated by the addition of 10 μL of CDK-2/Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The $K_i$ values were determined from the rate data as a function of inhibitor concentration.

Compounds of the present invention were found to inhibit CDK2.

Example 13

JAK Inhibition Assay

Compound inhibition of JAK was assayed by the method described by G. R. Brown, et al, *Bioorg. Med. Chem. Lett.* 2000, vol. 10, pp 575–579 in the following manner. Into Maxisorb plates, previously coated at 4° C. with Poly (Glu, Ala, Tyr) 6:3:1 then washed with phosphate buffered saline 0.05% and Tween (PBST), was added 2 μM ATP, 5 mM $MgCl_2$, and a solution of compound in DMSO. The reaction was started with JAK enzyme and the plates incubated for 60 minutes at 30° C. The plates were then washed with PBST, 100 μL HRP-Conjugated 4G10 antibody was added, and the plate incubated for 90 minutes at 30° C. The plate was again washed with PBST, 100 μL TMB solution is added, and the plates were incubated for another 30 minutes at 30° C. Sulfuric acid (100 μL of 1M) was added to stop the reaction and the plate is read at 450 nm to obtain the optical densities for analysis to determine $IC_{50}$ values. Compounds of the present invention were shown to inhibit JAK3.

Example 14

ERK2 Inhibition Assay

Compounds were assayed for the inhibition of ERK2 by a spectrophotometric coupled-enzyme assay (Fox et al *Protein Sci.* 1998, 7, 2249). In this assay, a fixed concentration of activated ERK2 (10 nM) was incubated with various concentrations of a compound of the present invention in DMSO (2.5%) for 10 min. at 30° C. in 0.1 M HEPES buffer (pH 7.5), containing 10 mM $MgCl_2$, 2.5 mM phosphoenolpyruvate, 200 μM NADH, 150 μg/ml pyruvate kinase, 50 μg/ml lactate dehydrogenase, and 200 μM erktide peptide. The reaction was initiated by the addition of 65 μM ATP. The rate of decrease of absorbance at 340 nM was monitored. The $K_i$ values were determined from the rate data as a function of inhibitor concentration.

Compounds of the present invention were found to inhibit ERK2.

Example 15

ERK2 Inhibition: Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 μL. The cells are allowed to attach to the plate by incubating at 37° C. for 2 hours. A solution of test compound is prepared in complete media by serial dilution to obtain the following concentrations: 20 μM, 6.7 μM, 2.2 μM, 0.74 μM, 0.25 μM, and 0.08 μM. The test compound solution (50 μL) is added to each of 72 cell-containing wells. To the 12 remaining cell-containing wells, only complete media (200 μL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 μCi/mL in RPMI medium then 20 μL of this solution is added to each well. The plates are further incubated at 37° C. for 8 hours then harvested and analyzed for $^3$H-thymidine uptake using a liquid scintillation counter.

Example 16

ERK1 Inhibition Assay

Compounds are assayed for the inhibition of ERK1 by a spectrophotometric coupled-enzyme assay (Fox et al (1998) *Protein Sci* 7, 2249). In this assay, a fixed concentration of activated ERK1 (20 nM) is incubated with various concentrations of the compound in DMSO (2.0%) for 10 minutes at 30° C. in 0.1 M HEPES buffer, pH 7.6, containing 10 mM $MgCl_2$, 2.5 mM phosphoenolpyruvate, 200 μM NADH, 30 μg/mL pyruvate kinase, 10 μg/mL lactate dehydrogenase, and 150 μM erktide peptide. The reaction is initiated by the addition of 140 μM ATP (20 μL). The rate of decrease of absorbance at 340 nM is monitored. The $K_i$ is evaluated from the rate data as a function of inhibitor concentration.

Example 17

GSK-3 Inhibition Assay

Compounds of the present invention were screened for their ability to inhibit GSK-3β(AA 1–420) activity using a standard coupled enzyme system (Fox et al., *Protein Sci.* 1998, 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of the present invention. The assay stock buffer solution (175 μl) was incubated in a 96 well plate with 5 μl of the test compound of the present invention at final concentrations spanning 0.002 μM to 30 μM at 30° C. for 10 min. Typically, a 12 point titration was conducted by preparing serial dilutions (from 10 mM compound stocks) with DMSO of the test compounds of the present invention in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the present invention were found to inhibit GSK3.

Example 18

ROCK Inhibition Assay

Compounds of the present invention were screened for their ability to inhibit ROCK using a standard coupled enzyme assay (Fox et al., *Protein Sci.* 1998, 7, 2249). Reactions were carried out in 100 mM HEPES (pH 7.5), 10 mM $MgCl_2$, 25 mM NaCl, 1 mM DTT and 1.5% DMSO. Final substrate concentrations in the assay were 13 μM ATP (Sigma chemicals) and 200 μM peptide (American Peptide, Sunnyvale, Calif). Assays were carried out at 30° C. and 200 nM ROCK. Final concentrations of the components of the coupled enzyme system were 2.5 mM phosphoenolpyruvate, 400 μM NADH, 30 μg/ml pyruvate kinase and 10 μg/ml lactate dehydrogenase.

An assay stock buffer solution was prepared containing all of the reagents listed above, with the exception of ROCK, DTT, and the test compound of interest of the present invention. 56 μl of the test reaction was placed in a 384 well plate followed by addition of 1 μl of 2 mM DMSO stock containing the test compound of the present invention (final compound concentration 30 μM). The plate was preincubated for about 10 minutes at 30° C. and the reaction initiated by addition of 10 μl of enzyme (final concentration 100 nM). Rates of reaction were obtained using a BioRad Ultramark plate reader (Hercules, Calif.) over a 5 minute read time at 30° C. Compounds of the present invention showing >50% inhibition versus standard wells containing DMSO, but no compound, were titrated and $IC_{50}$'s determined using a similar protocol.

Compounds of the present invention were found to be inhibitors of ROCK.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

What is claimed is:

1. A compound of formula I:

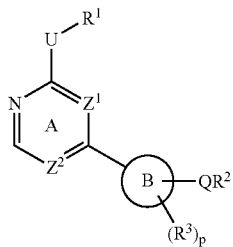

I or a pharmaceutically acceptable salt thereof, wherein:
Ring B is selected from

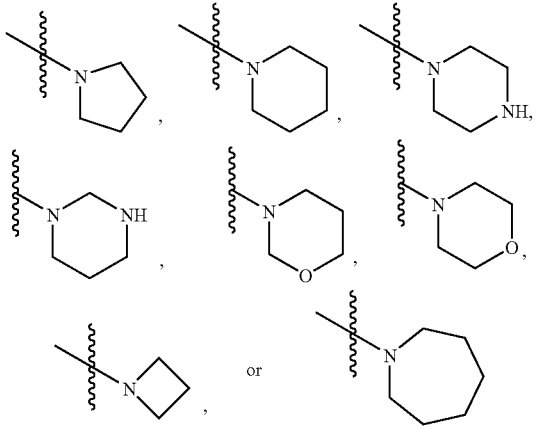

$Z^1$ is nitrogen;
$Z^2$ is $C\text{-}T_{(m)}R^y$, wherein $T_{(m)}R^y$ is $N(R)_2$, halogen, OH, 3–6 membered carbocyclyl, or an optionally substituted group selected from $C_{1-6}$ aliphatic, a 6 membered aryl ring, or a 5–6 membered heteroaryl ring having 1–3 heteroatoms independently selected from nitrogen, oxygen, or sulfur;
Q is selected from a saturated or unsaturated $C_{1-4}$ alkylidene chain wherein:
up to two methylene units of the chain are optionally and independently replaced by —C(O)—, —C(O)C(O)—, —C(O)NR—, —C(O)NRNR—, —CO$_2$—, —OC(O)—, —O—, —NRC(O)NR—, —OC(O)NR—, —NRNR—, —NRC(O)—, —S—, —SO—, —SO$_2$—, —NR—, —SO$_2$NR—, or —NRSO$_2$—;
each R is independently selected from hydrogen or an optionally substituted $C_{1-6}$ aliphatic group, or:
two R on the same nitrogen are taken together with the nitrogen to form a 5–8 membered heterocyclyl or heteroaryl ring having 1–3 heteroatoms independently selected from nitrogen, oxygen, or sulfur;
each Ar is an optionally substituted ring selected from a 6–10 membered aryl ring, a 5–10 membered heteroaryl ring having 1–4 heteroatoms independently selected from nitrogen, oxygen, or sulfur, or a 3–10 membered heterocyclyl ring having 1–4 heteroatoms independently selected from nitrogen, oxygen, or sulfur;
$R^1$ selected from CN, R, Ar, —(CH$_2$)$_y$CH(R$^4$)R$^5$, or —(CH$_2$)$_y$CH(R$^4$)CH(R$^5$)$_2$;
each y is independently 0–6;
U is selected from a —O—, —S—, —N(R)—, or a $C_{1-6}$ alkylidene chain wherein up to two methylene units of U are optionally and independently replaced by —O—, —S—, —SO—, —SO$_2$—, —N(R)SO$_2$—, —SO$_2$N(R)—, —N(R)—, —CO—, —CO$_2$—, —N(R)CO—, —N(R)C(O)O—, —N(R)CON(R)—, —N(R)SO$_2$N(R)—, —N(R)N(R)—, —C(O)N(R)—, or —OC(O)N(R)—;
$R^2$ is selected from (CH$_2$)$_y$CH(R$^5$)$_2$ or (CH$_2$)$_y$CH(R$^4$)CH(R$^5$)$_2$;
y is 0–6;
$R^3$ is selected from oxo, R, F, Cl, N(R)$_2$, OR, SR, NRC(O)R, NRC(O)N(R)$_2$, C(O)N(R)$_2$, SO$_2$R, NRSO$_2$R, C(O)R, CN, SO$_2$N(R)$_2$, N(R)O, ON(R), or N(R)N(R);
p is 0–4;
$R^4$ is selected from R, (CH$_2$)$_w$OR, (CH$_2$)$_w$N(R)$_2$, or (CH$_2$)$_w$SR;
w is 0–4; and
each $R^5$ is independently selected from optionally substituted $C_{1-6}$ aliphatic, Ar, (CH$_2$)$_w$OR, CO$_2$R, (CH$_2$)$_w$N(R)$_2$, N(Ar)(R), (CH$_2$)$_w$SR, NRC(O)R, NRC(O)N(R)$_2$, C(O)N(R)$_2$, SO$_2$R, NRSO$_2$R, C(O)R, CN, or SO$_2$N(R)$_2$.

2. The compound according to claim 1, wherein Ring B is selected from

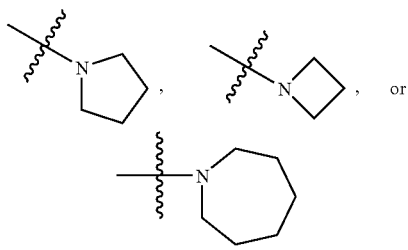

3. The compound according to claim 1, wherein Ring B is selected from

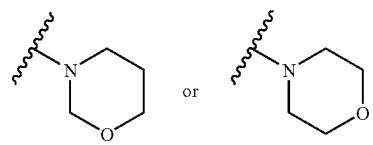

4. The compound according to claim 1, wherein:
(T)$_m$R$^y$ is selected from N(R)$_2$, halogen, OH, 3–6 membered carbocyclyl, or an optionally substituted group selected from $C_{1-6}$ aliphatic, a 6 membered aryl ring, or a 5–6 membered heteroaryl ring having 1–3 heteroatoms independently selected from nitrogen, oxygen, or sulfur;

$R^1$ is selected from hydrogen, R, optionally substituted 3–7 membered carbocyclyl or an optionally substituted group selected from a 3–6 membered heterocyclic ring having 1–3 heteroatoms independently selected from nitrogen, oxygen, or sulfur, or a 5–6 membered aryl or heteroaryl ring having 1–3 heteroatoms independently selected from nitrogen, oxygen, or sulfur;

U is selected from —$CH_2$—, —O—, —NR—, —NHC(O)—, or —$NHCO_2$—;

Q is a $C_{1-4}$ alkylidene chain wherein one or two methylene units of Q are independently replaced by —C(O)—, —OC(O)—, —C(O)NH—, —OC(O)NH—, —$SO_2$—, —$SO_2$NH—, —NHC(O)—, or —$NHSO_2$—;

$R^2$ is —$(CH_2)_yCH(R^5)_2$; and each $R^5$ group is independently selected from optionally substituted $C_{1-4}$ aliphatic, $C_{5-6}$ cycloalkyl, phenyl, a 5–9 membered heteroaryl ring having 1–2 heteroatoms independently selected from nitrogen, oxygen, or sulfur, or a 5–6 membered heterocyclic ring having 1–2 heteroatoms independently selected from nitrogen, oxygen, or sulfur.

5. The compound according to claim 1, wherein:

$(T)_mR^y$ is selected from $N(R)_2$, halogen, OH, 3–6 membered carbocyclyl, or an optionally substituted group selected from $C_{1-6}$ aliphatic, a 6 membered aryl ring, or a 5–6 membered heteroaryl ring having 1–3 heteroatoms independently selected from nitrogen, oxygen, or sulfur;

$R^1$ is —$(CH_2)_yCH(R^5)_2$;

U is selected from a valence bond, —$CH_2$—, —O—, —NR—, —NHC(O)—, or —$NHCO_2$—;

Q is a $C_{1-4}$ alkylidene chain wherein one or two methylene units of Q are independently replaced by —C(O)—, —OC(O)—, —C(O)NH—, —OC(O)NH—, —$SO_2$—, —$SO_2$NH—, —NHC(O)—, or —$NHSO_2$—;

$R^2$ is —$(CH_2)_yCH(R^5)_2$; and each $R^5$ group is independently selected from optionally substituted $C_{1-4}$ aliphatic, $C_{5-6}$ cycloalkyl, phenyl, a 5–9 membered heteroaryl ring having 1–2 heteroatoms independently selected from nitrogen, oxygen, or sulfur, or a 5–6 membered heterocyclic ring having 1–2 heteroatoms independently selected from nitrogen, oxygen, or sulfur.

6. The compound according to claim 1, wherein:

$(T)_mR^y$ is selected from $N(R)_2$, halogen, OH, 3–6 membered carbocyclyl, or an optionally substituted group selected from $C_{1-6}$ aliphatic, a 6 membered aryl ring, or a 5–6 membered heteroaryl ring having 1–3 heteroatoms independently selected from nitrogen, oxygen, or sulfur;

$R^1$ is selected from hydrogen, R, optionally substituted 3–7 membered carbocyclyl or an optionally substituted group selected from a 3–6 membered heterocyclic ring having 1–3 heteroatoms independently selected from nitrogen, oxygen, or sulfur, or a 5–6 membered aryl or heteroaryl ring having 1–3 heteroatoms independently selected from nitrogen, oxygen, or sulfur;

U is selected from —$CH_2$—, —O—, —NR—, —NHC(O)—, or —$NHCO_2$—;

Q is a $C_{1-4}$ alkylidene chain wherein one or two methylene units of Q are independently replaced by —C(O)—, —OC(O)—, —C(O)NH—, —OC(O)NH—, —$SO_2$—, —$SO_2$NH—, —NHC(O)—, or —$NHSO_2$—;

R is —$(CH_2)_yCH(R^5)_2$; and each $R^5$ group is independently selected from —OR, —$CO_2R$, —$(CH_2)_wN(R)_2$, or —N(Ar)(R).

7. The compound according to claim 1, wherein:

$(T)_mR^y$ is selected from $N(R)_2$, halogen, OH, 3–6 membered carbocyclyl, or an optionally substituted group selected from $C_{1-6}$ aliphatic, a 6 membered aryl ring, or a 5–6 membered heteroaryl ring having 1–3 heteroatoms independently selected from nitrogen, oxygen, or sulfur;

$R^1$ is —$(CH_2)_yCH(R^5)_2$;

U is selected from —$CH_2$—, —O—, —NR—, —NHC(O)—, or —$NHCO_2$—;

Q is a $C_{1-4}$ alkylidene chain wherein one or two methylene units of Q are independently replaced by —C(O)—, —OC(O)—, —C(O)NH—, —OC(O)NH—, —$SO_2$—, —$SO_2$NH—, —NHC(O)—, or —$NHSO_2$—;

$R^2$ is —$(CH_2)_yCH(R^5)_2$; and each $R^5$ group is independently selected from —OR, —$CO_2R$, —$(CH_2)_wN(R)_2$, or —N(Ar)(R).

8. The compound according to claim 1, wherein said compound is selected from the following compounds:

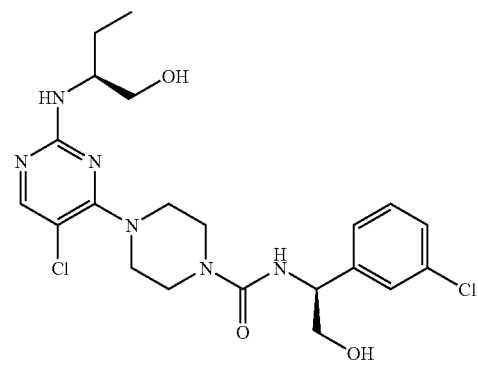

I-1

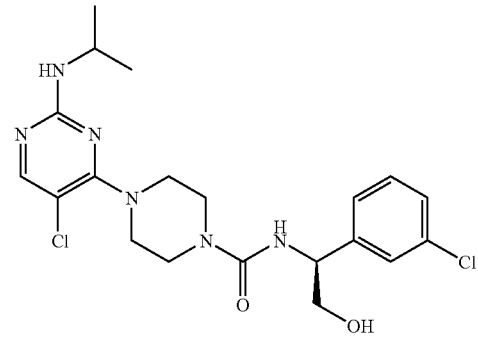

I-2

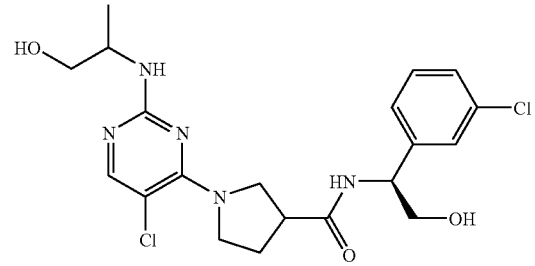

I-7

-continued

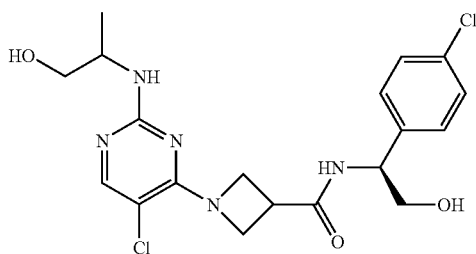

I-9 and

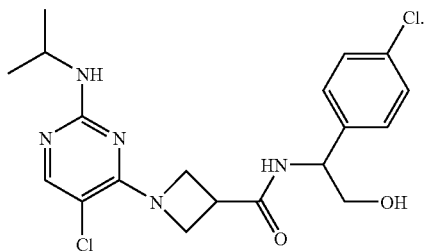

I-12

9. A composition comprising a compound according to claim 1, and a pharmaceutically acceptable carrier, adjuvant, or vehicle.

10. The composition according to claim 9, additionally comprising a therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

11. A method of inhibiting CDK2, ERK2, GSK-3, or ROCK protein kinase activity in vitro in a biological sample selected from cell cultures or extracts thereof, biopsied material obtained from a mammal or extracts thereof, saliva, urine, feces, semen, or tears, said method comprising the step of contacting said biological sample with:
   a) a compound according to claim 1; or
   b) a composition according to claim 9.

12. A method of treating, or lessening the severity of, melanoma, colon cancer, breast cancer, gastric cancer, ovarian cancer, cervical cancer, lung cancer, renal cancer, prostate cancer, bladder cancer, or pancreatic cancer, in a patient in need thereof wherein said method comprises administering to said patient a composition according to claim 9.

13. The method according to claim 12, wherein said method is used to treat or lessen the severity of melanoma, or a cancer selected from breast cancer, colon cancer, or pancreatic cancer.

* * * * *